United States Patent
Chang et al.

(10) Patent No.: US 10,919,908 B2
(45) Date of Patent: Feb. 16, 2021

(54) THIENOPYRIMIDINONE DERIVATIVE AND APPLICATION THEREOF IN PREPARING ANTICANCER DRUG

(71) Applicant: Henan Genuine Biotech Co., Ltd., Pingdingshan (CN)

(72) Inventors: Junbiao Chang, Zhengzhou (CN); Jinfa Du, Zhengzhou (CN)

(73) Assignee: HENAN GENUINE BIOTECH CO., LTD., Pingdingshan (CN)

( * ) Notice: Subject to any disclaimer, the term of this patent is extended or adjusted under 35 U.S.C. 154(b) by 0 days.

(21) Appl. No.: 16/503,656

(22) Filed: Jul. 5, 2019

(65) Prior Publication Data
US 2019/0330230 A1    Oct. 31, 2019

Related U.S. Application Data

(63) Continuation-in-part of application No. PCT/CN2017/117610, filed on Dec. 21, 2017.

(30) Foreign Application Priority Data

Jan. 5, 2017    (CN) .......................... 2017 1 0006807

(51) Int. Cl.
*A61P 35/00* (2006.01)
*C07D 495/04* (2006.01)
*A61K 45/06* (2006.01)

(52) U.S. Cl.
CPC ............ *C07D 495/04* (2013.01); *A61P 35/00* (2018.01); *A61K 45/06* (2013.01)

(58) Field of Classification Search
CPC ...................................................... A61P 35/00
See application file for complete search history.

(56) References Cited

PUBLICATIONS

Han, H. "Targeted Prodrug Design to Optimize Drug Delivery." AAPS Pharmsci. (2000), vol. 2 (1) article 6, pp. 1-11. (Year: 2000).*
Ettmayer, P., et al. "Lessons Learned from Marketed and Investigational Prodrugs." J. Med. Chem. (2004) 47(10), pp. 2393-2404. (Year: 2004).*
Testa, B. "Prodrug research: futile or fertile?" Biochem. Pharm. (2004) 68, pp. 2097-2106. (Year: 2004).*
American Chemical Society Chemical Abstract Service. RN #: 1799641-48-7, entered into STN on Jul. 16, 2015. (Year: 2015).*

* cited by examiner

*Primary Examiner* — John S Kenyon
(74) *Attorney, Agent, or Firm* — Matthias Scholl P.C.; Matthias Scholl

(57) ABSTRACT

The disclosure relates to a thienopyrimidinone derivative, or a pharmaceutically acceptable prodrug, salt, and solvate thereof. The derivative has the formula (I), where R represents hydrogen (H) or deuterium (D); $R^1$ and $R^2$ independently, at each occurrence, represent H, D, F, Cl, I, cyano group (CN), or $N_3$, and when R represents H, $R^1$ and $R^2$ do not synchronously represent H; $R^3$, $R^4$ and $R^5$ independently, at each occurrence, represent an alkyl group, a cycloalkyl group, a heterocyclic group, an aromatic ring group, or a heteroaryl ring group, which are substituted or unsubstituted.

8 Claims, No Drawings

THIENOPYRIMIDINONE DERIVATIVE AND APPLICATION THEREOF IN PREPARING ANTICANCER DRUG

CROSS-REFERENCE TO RELATED APPLICATIONS

This application is a continuation-in-part of International Patent Application No. PCT/CN2017/117610 with an international filing date of Dec. 21, 2017, designating the United States, now pending, and further claims foreign priority benefits to Chinese Patent Application No. 201710006807.X filed Jan. 5, 2017. The contents of all of the aforementioned applications, including any intervening amendments thereto, are incorporated herein by reference. Inquiries from the public to applicants or assignees concerning this document or the related applications should be directed to: Matthias Scholl P C., Attn.: Dr. Matthias Scholl Esq., 245 First Street, 18th Floor, Cambridge, Mass. 02142.

BACKGROUND

The disclosure relates to a thienopyrimidinone derivative, or a pharmaceutically acceptable prodrug, salt, and solvate thereof.

Apoptosis is a form of programmed cell death that is a highly regulated and controlled. Out of control apoptosis leads to tumorigenesis.

Anti-apoptotic B-cell lymphoma 2 (Bcl-2) family proteins are associated with a variety of cancers, such as colon cancer, breast cancer, small cell lung cancer, non-small cell lung cancer, bladder cancer, ovarian cancer, prostate cancer, chronic lymphocytic leukemia, lymphoma, myeloma, acute marrow leukemia, and pancreatic cancer. Tumor development and chemotherapy resistance are related to the overexpression of the anti-apoptotic Bcl-2 family proteins. Myeloid cell leukemia 1 (Mcl-1) is a member of the anti-apoptotic Bcl-2 family and is overexpressed in many types of cancer. Mcl-1 is a pro-survival protein that allows cancer cells to escape the process of apoptosis. It has been confirmed that the Mcl-1 inhibitors have an antitumor effect.

The thienopyrimidinone derivatives belong to the family of Mcl-1 inhibitors. Typically, the thienopyrimidinone derivatives have the formula as follows:

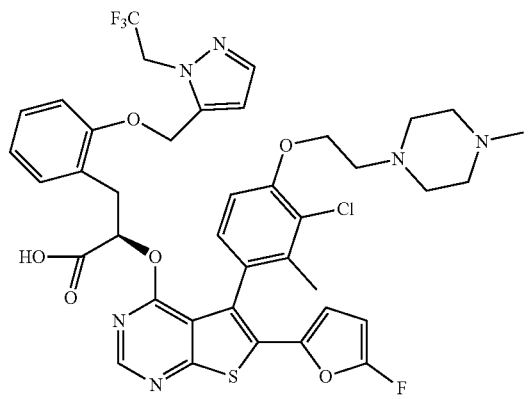

(II)

SUMMARY

One objective of the disclosure is to provides a Mcl-1 or Bcl-2 inhibitor and an application thereof.

Provided is a compound having a formula (I), or a pharmaceutically acceptable prodrug, salt, solvate thereof:

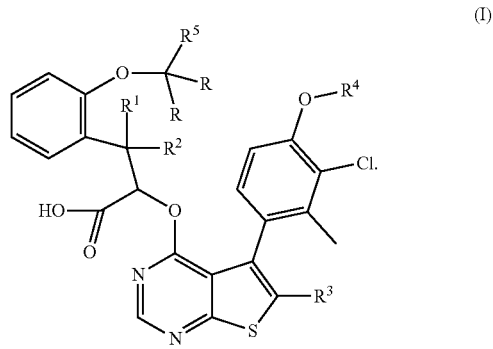

(I)

where R represents hydrogen (H) or deuterium (D); $R^1$ and $R^2$ independently, at each occurrence, represent H, D, F, Cl, I, cyano group (CN), or $N_3$, and when R represents H, $R^1$ and $R^2$ do not synchronously represent H; $R^3$, $R^4$ and $R^5$ independently, at each occurrence, represent an alkyl group, a cycloalkyl group, a heterocyclic group, an aromatic ring group (Ar), or a heteroaryl ring group, which are substituted or unsubstituted.

Particularly, $R^3$, $R^4$ and $R^5$ independently, at each occurrence, represent a $C_{1-5}$ alkyl group, a $C_{3-6}$ cycloalkyl group, a nitrogen-containing or oxygen-containing saturated or unsaturated five- or six-membered heterocyclic ring, or a phenyl group.

The compound can be a single stereoisomer or racemic mixture of the formula (I).

The compound can have the formula (III):

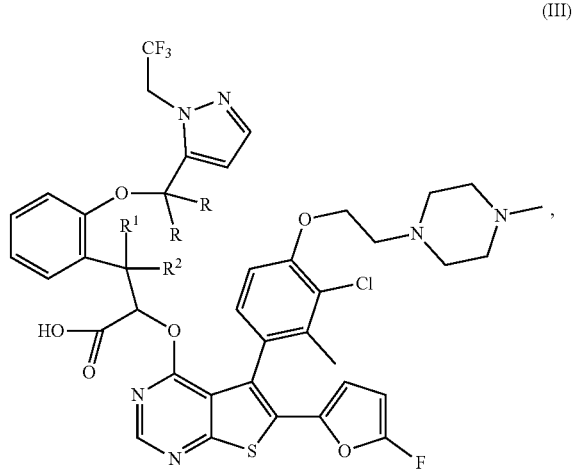

(III)

where R represents hydrogen (H) or deuterium (D); and $R^1$ and $R^2$ independently, at each occurrence, represent H, D, F, Cl, I, cyano group, or $N_3$, and when R represents H, and $R^1$ and $R^2$ do not synchronously represent H.

The compound can have the following formulas (IV-XI):
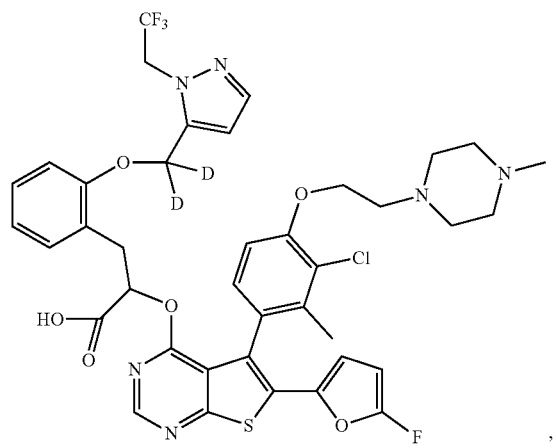
IV
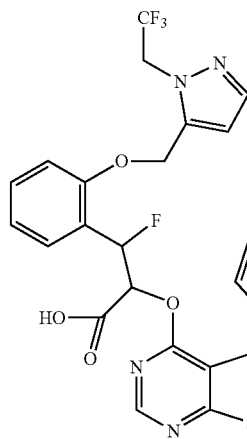
VII
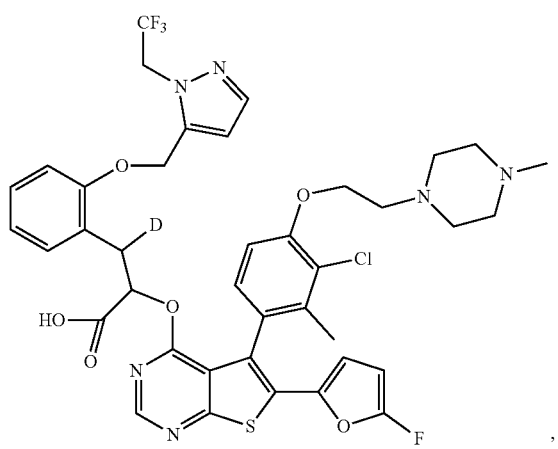
V
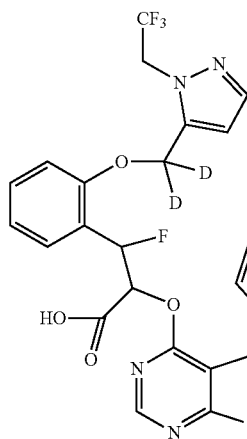
VIII
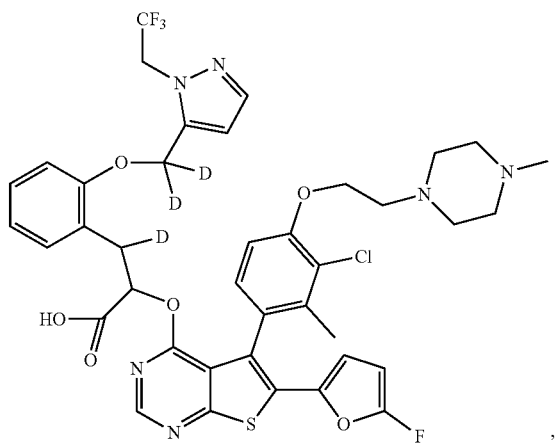
VI
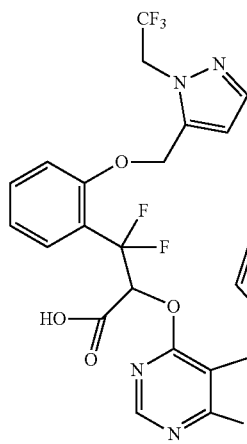
IX
,

X

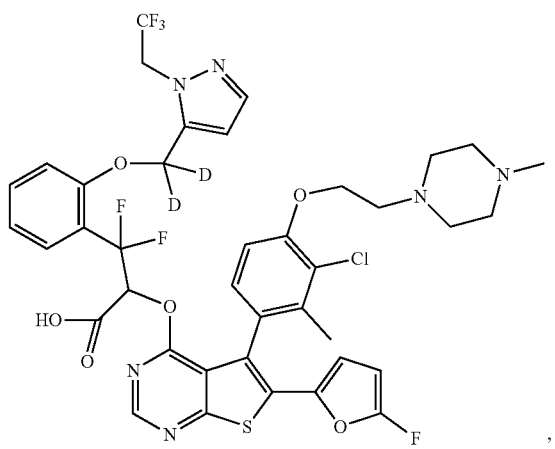

,

XI

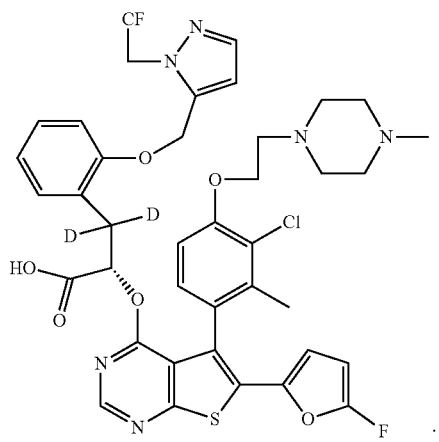

The salt of the compound (I) can be obtained by chemical reaction of the compound (I) with an acid. The acid can include, but is not limited to, p-toluenesulfonic acid, salicylic acid, tartaric acid, tartaric acid, ascorbic acid, maleic acid, benzene sulfonic acid, fumaric acid, gluconic acid, glucuronic acid, formic acid, glutamic acid, methane sulfonic acid, ethane sulfonic acid, lactic acid, oxalic acid, p-bromobenzene sulfonic acid, carbonic acid, citric acid, benzoic acid, malic acid, acetic acid; particularly, methane sulfonic acid.

The disclosure also provides a pharmaceutical composition comprising the compound having the formula (I), or a pharmaceutically acceptable prodrug, salt, solvate thereof, a pharmaceutically acceptable carrier, and a diluent.

The above pharmaceutical composition can further comprise an anticancer agent.

Also provided is a method of preparing a pharmaceutical composition for treatment of a tumor. The tumor can be acute myeloid leukemia, lymphoma and multiple myeloma, melanoma, lung and breast cancer, brain tumor, adenocarcinoma, liver cancer, colorectal cancer, medullary thyroid carcinoma, glioma, neuroblastoma, kidney tumor ovarian cancer, and prostate cancer.

One of the compounds of the disclosure can be prepared by the following methods:

(1) A compound a-1 reacts with a compound a-2 to form an intermediate a-3.

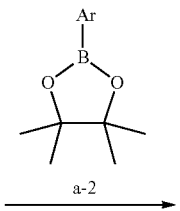

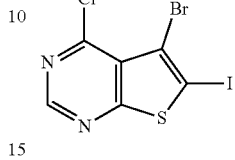

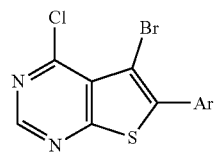

where Ar is an optionally substituted aromatic ring or a heterocyclic ring.

(2) The compound a-3 reacts with an intermediate a-4 to form an intermediate a-5.

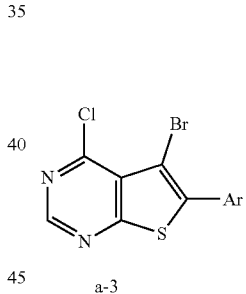

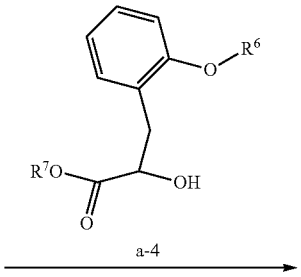

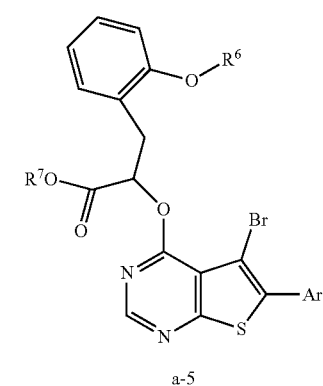

where Ar is defined as above; and $R^6$ and $R^7$ are an optionally substituted alkyl group, aryl group or heterocyclic or heteroaryl group.

(3) The compound a-5 reacts with an intermediate a-6 to form an intermediate a-7.

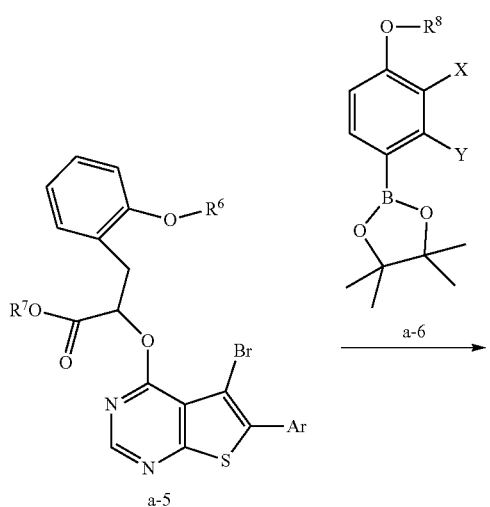

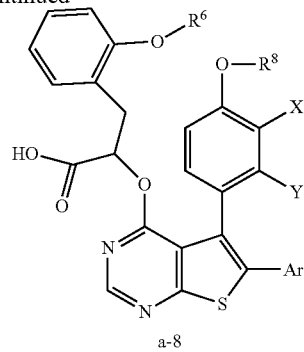

where Ar, R6, R7, and R8 are defined as above.

Compared with conventional compound (II), the compound having the formula (I) of the disclosure exhibits better physical properties, stronger inhibition against the Mcl-1 activity and more stable characteristics.

DETAILED DESCRIPTION

Example 1

Preparation of Compounds (4) and (5)

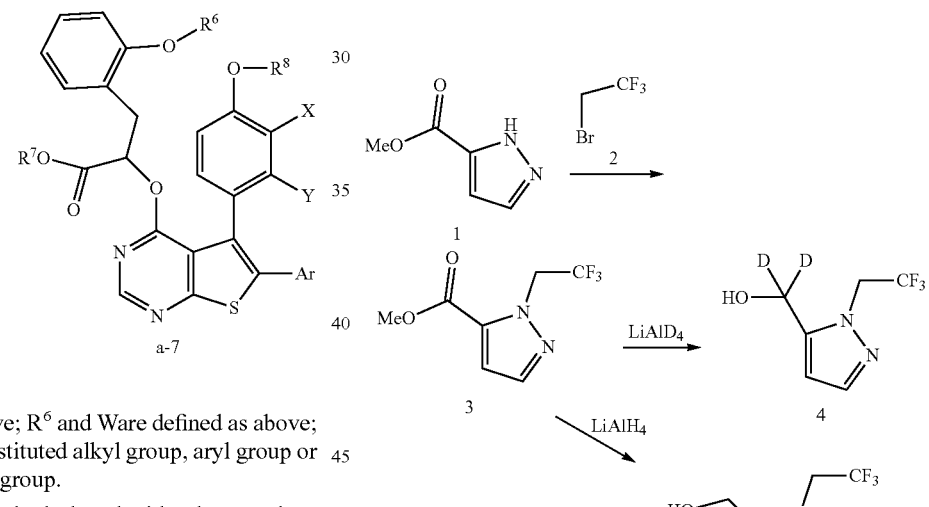

where Ar is defined as above; $R^6$ and W are defined as above; and $R^8$ is an optionally substituted alkyl group, aryl group or heterocyclic or heteroaryl group.

(4) The compound a-7 is hydrolyzed with a base such as LiOH, KOH or NaOH to obtain the compound a-8.

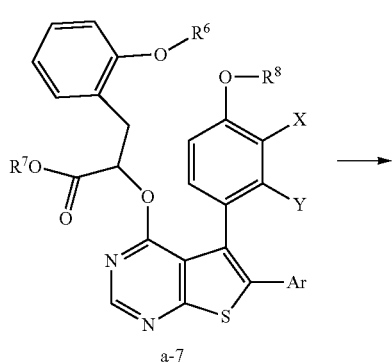

A. Compound 3: the compound 1 (1.26 g, 10 mmol) was dissolved in THF (20 mL) in the presence of nitrogen atmosphere, and cooled to 0° C. in an ice water bath; NaH (60%, 0.6 g, 15 mmol) was added and the mixture was stirred 15 min; subsequently, a mixed solution of compound 2 (2.44 g, 15 mmol) and THF (5 mL) was added into the above solution with a syringe. After stirring the reaction mixture for 3 h, $CH_2Cl_2$ was added; and the mixture was washed with brine and the organic phase was dried over $Na_2SO4$; after the organic solvent was evaporated, the residue was mixed with toluene (20 mL). And after evaporation to dryness, a crude product 3 was obtained, which was used in the next step without purification. ES/MS: m/z: 209 $[M+H]^+$.

B. Compound 4: the compound 3 (1.04 g, 5 mmol) was dissolved in THF (20 mL) in the presence of nitrogen, and the resulting solution was cooled to −78° C. in a dry ice-acetone bath. A mixture of $LiAlD_4$ (190 mg, 5 mmol) and THF (10 mL) was added to the reaction mixture with a syringe. The reaction temperature was controlled at −50° C., and the reaction solution was stirred for 30 min. After the addition of EtOAc (50 mL), the mixture was washed with brine and then the organic phase was dried over $Na_2SO_4$. Finally, the organic solvent was evaporated, and the residue was purified (0-50% EtOAc/hexane) by silica gel column chromatography to obtain a compound 4. m/z: 183 $[M+H]^+$.

C. Compound 5: the same method as for the preparation of the compound 4 was employed except that the compound 3 was reduced to obtain a compound 5. m/z: 181 $[M+H]^+$.

Example 2

Preparation of Compounds (7) and (8)

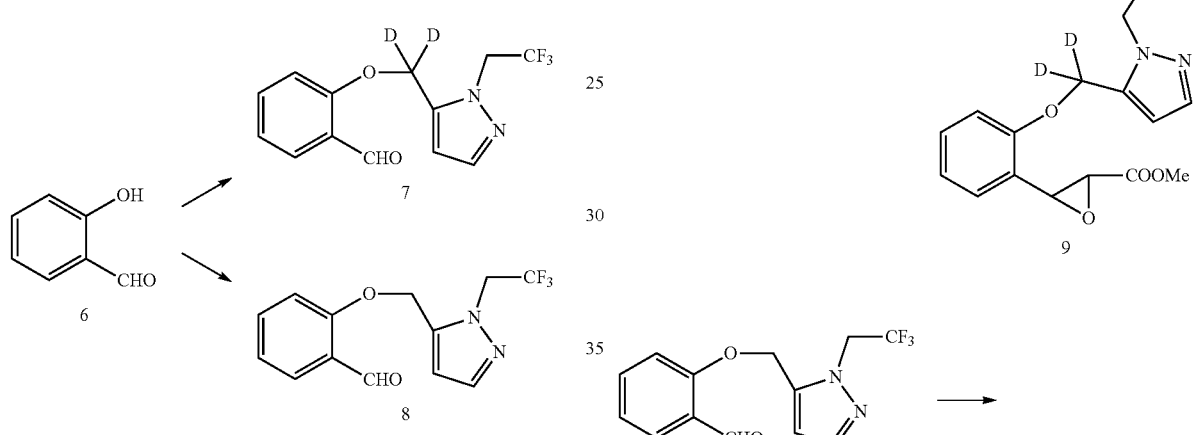

A. Compound 7: the compound 4 (182 mg, 1.0 mmol), 2-hydroxybenzoate 6 (122 mg, 1.0 mmol) and $PPh_3$ (314 mg, 1.2 mmol) were dissolved in dry toluene (10 mL). Then the azodiyldipiperidine (ADDP, 302 mg, 1.2 mmol) was added and the reaction mixture was stirred at 50° C. for 24 h. After the addition of EtOAc (50 mL), the mixture was washed with brine and then the organic phase was dried over $Na_2SO_4$. Finally, the organic solvent was evaporated, and the residue was purified (0-50% EtOAc/hexane) by silica gel column chromatography to obtain a compound 7. m/z: 287 $[M+H]^+$. The compound 7 can be stored at −20° C. for later use.

B. Compound 8: the same method as for the preparation of the compound 7 was employed except that the compound 5 was condensed with o-hydroxybenzaldehyde to obtain Compound 8.

C. Intermediate compounds 7 or 8 can also be prepared by the following method:

The compound 4 or 5 (1.0 mmol), methyl 2-hydroxybenzoate (152 mg, 1.0 mmol) and $PPh_3$ (314 mg, 1.2 mmol) were dissolved in dry toluene (10 mL). Then the azodiyldipiperidine (ADDP, 302 mg, 1.2 mmol) was added and the reaction mixture was stirred at 50° C. for 24 h. After the addition of EtOAc (50 mL), the mixture was washed with brine and then the organic phase was dried over $Na_2SO_4$. Finally, the organic solvent was evaporated, and the residue was purified (0-50% EtOAc/hexane) by silica gel column chromatography to obtain the corresponding methyl ester intermediate. The methyl ester was reduced by DIBAL to obtain the compound 7 or 8, respectively.

Example 3

Preparation of Compounds (9) and (10) (Chinese Journal of Synthetic Chemistry 2010, 18, 215-218)

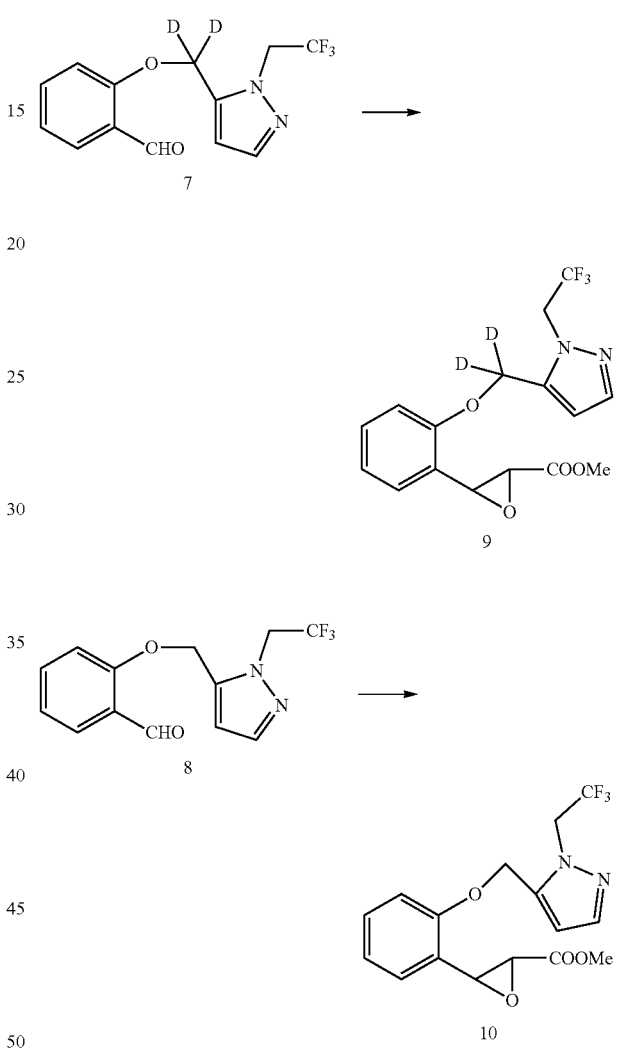

A. Compound 9: under a nitrogen atmosphere and an ice water bath, a mixture of compound 7 (2.86 g, 10.0 mmol), ethyl chloroacetate (1.84 g, 15.0 mmol) and $CH_2Cl_2$ (20 mL) was added to the reaction vessel. Freshly prepared 1 M/L sodium methoxide (30 mL, 30.0 mmol) was added dropwise during the stirring. After the dropwise addition, the mixture was stirred at 20° C. for 24 h. The filtrate obtained after filtration was subjected to reduced pressure and evaporated to dryness. Finally, the residue was purified (0-50% EtOAc/hexane) by silica gel column chromatography to obtain a compound 9. ES/MS: m/z: 359 $[M+H]^+$.

B. Compound 10: the same method as for the preparation of the compound 9 was employed except that the Compound 8 was reacted with ethyl chloroacetate to obtain a compound 10. ES/MS: m/z: 357 $[M+H]^+$.

Example 4

Preparation of Compounds Rac-11, (2S, 3R)-12 and (2R, 3S)-13

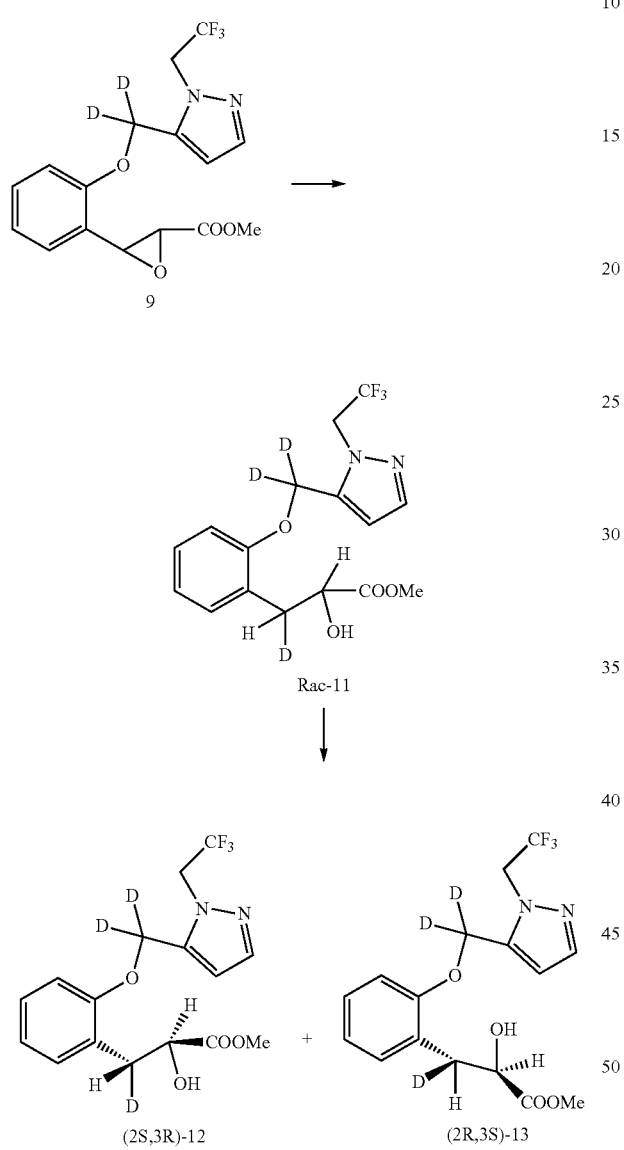

A. Compound Rac-11: the compound 9 was dissolved in methanol, after which 5% Pd/C was added thereto. The mixture was stirred for 2-5 h under a helium (D2) atmosphere (the progress of the reaction was monitored to avoid side reactions). After the reaction, the mixture was filtered, and the organic solvent was evaporated. Finally, the residue was purified (0-100% EtOAc/hexane) by silica gel column chromatography to obtain Compound Rac-11. ES/MS: m/z: 362 [M+H]$^+$.

B. Compounds (2S, 3R)-12 and (2R,3S)-13: Rac-11 was separated by chiral column to obtain (2S,3R)-12 and (2R, 3S)-13, respectively.

Example 5

Preparation of the Compounds Rac-14, (2S, 3R)-15 and (2R, 3S)-16

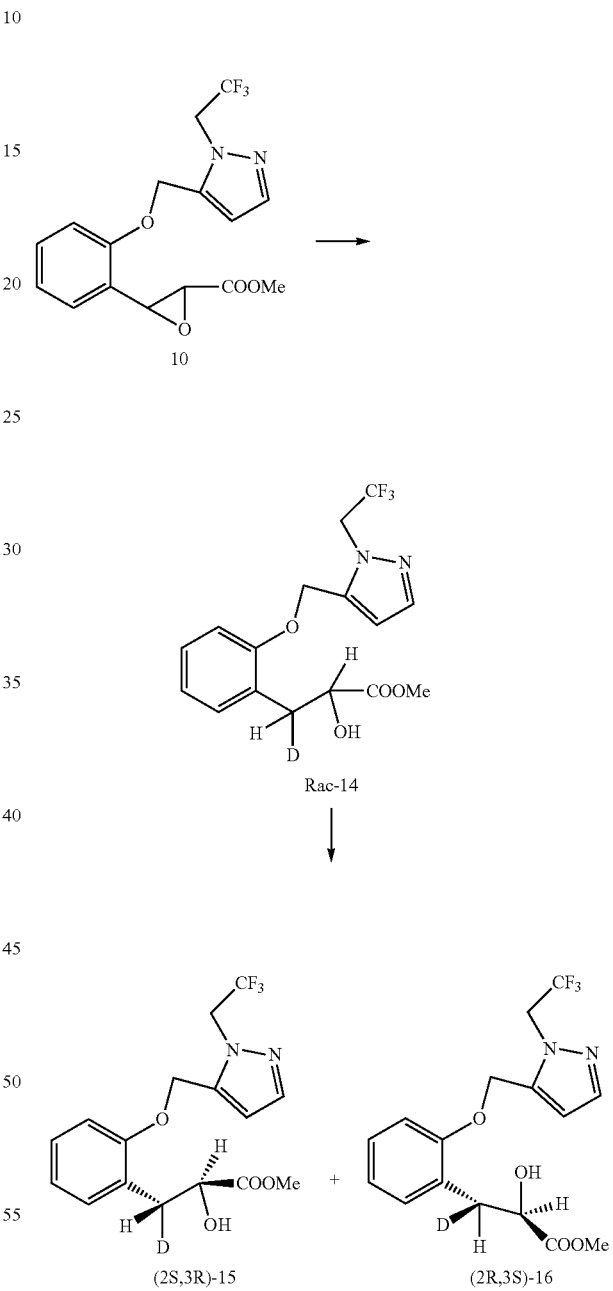

A. Compound Rac-14: according to the same method for the preparation of Compound Rac-11, the compound 10 was deuterated to obtain the compound Rac-14. ES/MS: m/z: 360 [M+H]$^+$.

B. Compounds (2S, 3R)-15 and (2R,3S)-16: Rac-14 was separated by chiral chromatography to obtain (2S,3R)-15 and (2R,3S)-16, respectively.

Example 6

Preparation of Compounds Rac-17, (2S)-18 and (2R)-19 (Org. Lett. 2010, 12, 2936-2939)

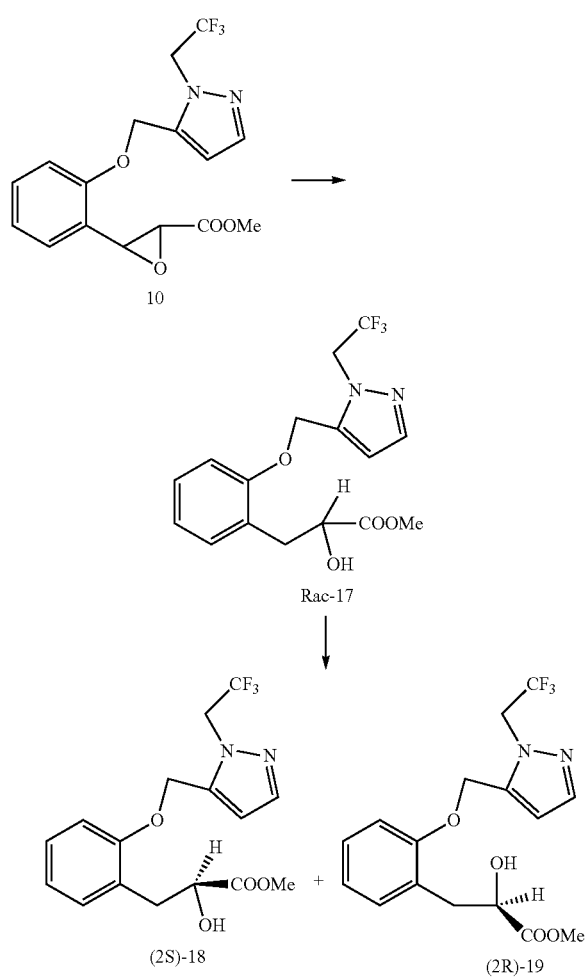

A. Compound Rac-17: according to the same method for the preparation of Compound Rac-11, the compound 10 was catalytically hydrogenated to obtain the Compound Rac-17. ES/MS: m/z: 359 [M+H]$^+$.

B. Compounds (2S)-18 and (2R)-19: Rac-17 was separated by chiral column to obtain (2S)-18 and (2R)-19, respectively.

Example 7

Preparation of the Compounds Rac-20, (2S)-21 and (2R)-22

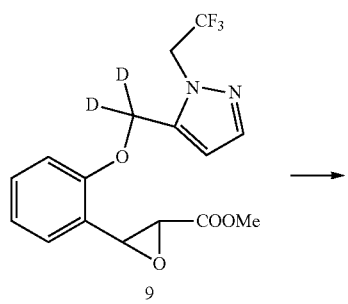

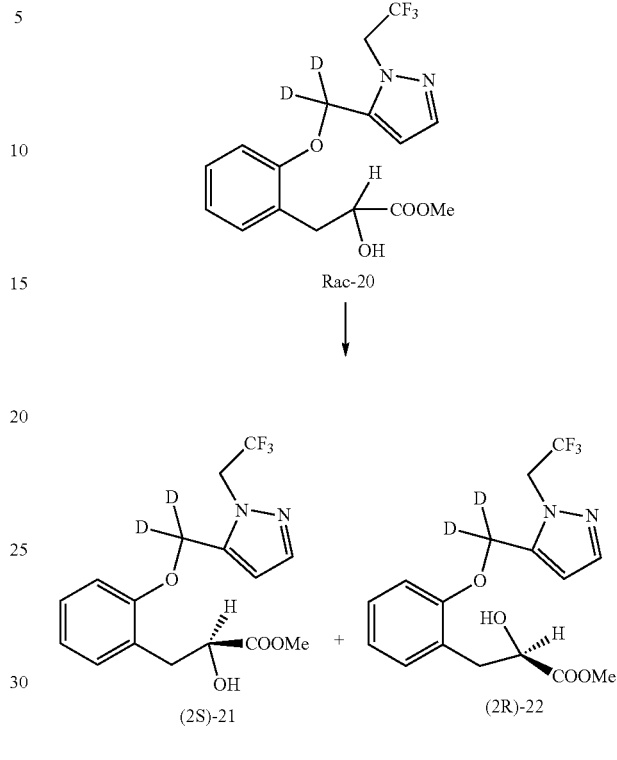

A. Compound Rac-20: according to the same method for the preparation of Compound Rac-11, the compound 9 was catalytically hydrogenated to obtain the compound Rac-20. m/z: 361 [M+H]$^+$.

B. Compounds (2S)-21 and (2R)-22: Rac-20 was separated by chiral column to obtain (2S)-21 and (2R)-22, respectively.

Example 8

Preparation of the Compounds Rac-23, (2R, 3R)-24 and (2S, 3S)-25 (Org. Lett. 2010, 12, 2936-2939)

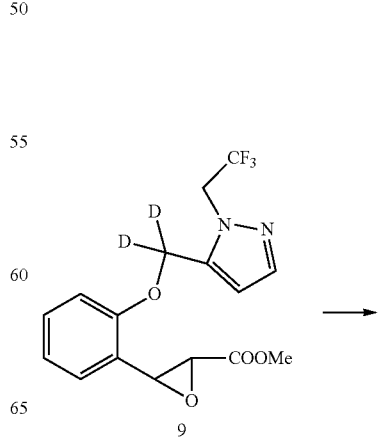

15
-continued

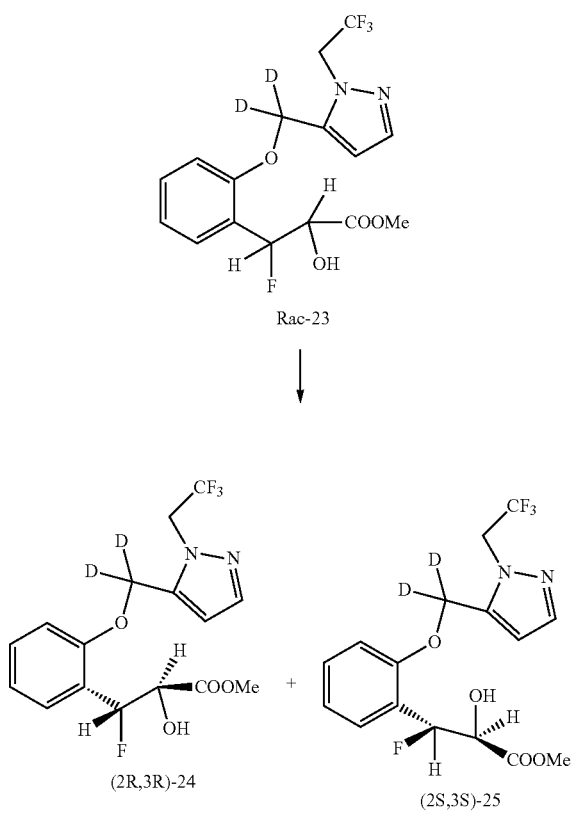

Rac-23

(2R,3R)-24 + (2S,3S)-25

A. Compound Rac-23: after dissolving Compound 9 in CH$_2$Cl$_2$, BF$_3$.OEt$_2$ was added thereto at 0° C. The reaction mixture was stirred at −20° C. for 30 min, washed with water and dried over Na$_2$SO$_4$. After the organic solvent was evaporated, the residue was purified (0-100% EtOAc/hexane) by silica gel column chromatography to obtain Compound Rac-23. ES/MS: m/z: 379 [M+H]$^+$.

Example 9

Preparation of the Compounds Rac-26, (2S, 3R)-27 and (2R, 3S)-28 (Org. Lett. 2010, 12, 2936-2939)

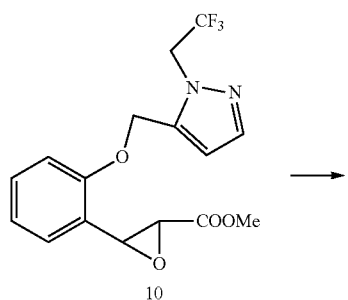

10

16
-continued

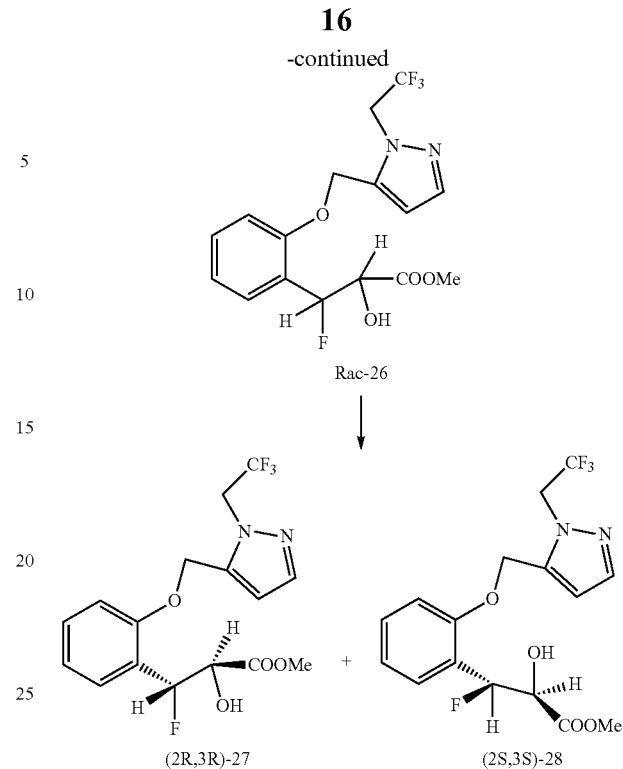

Rac-26

(2R,3R)-27 + (2S,3S)-28

A. Compound Rac-26: the same method as for the preparation of the compound Rac-23 was employed except that the compound 10 was fluorinated to obtain Rac-26. ES/MS: m/z: 377 [M+H]$^+$.

B. Compounds (2R, 3R)-27 and (2S, 3S)-28: Rac-26 were separated by chiral column to obtain (2R, 3R)-27 and (2S, 3S)-28, respectively.

C. Asymmetric epoxidation of (2R, 3R)-27 and (2S, 3S)-28 with cis- or trans-3-[(2-methoxy)phenyl]-2,3-propenol, reoxidation and ring opening, to yield 2-hydroxy-3-fluoro-3-phenyl with 4 different optical isomers.

Example 10

Preparation of Compound 31 (Tetrahedron 2004, 60, 7731-7742)

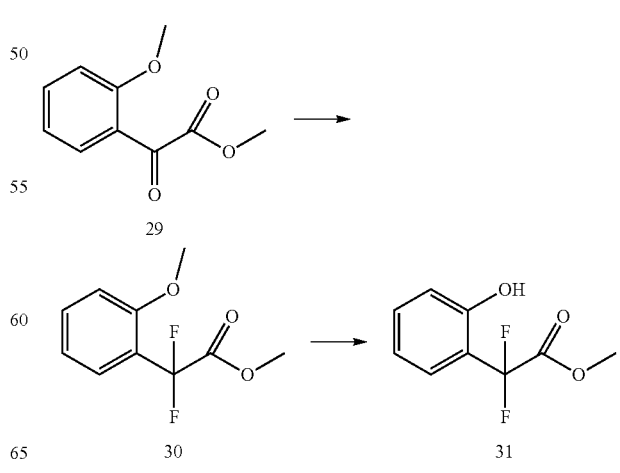

A. Compound 29 (388 mg, 2 mmol) was dissolved in THF (20 mL) under nitrogen atmosphere. DAST or Deoxo-Fluor (5 mmol) was added at 0° C., and the reaction mixture was stirred at 40° C. for 24 h. After the addition of EtOAc (50 mL), the mixture was washed with brine and then the organic phase was dried over Na$_2$SO$_4$. Finally, the organic solvent was evaporated, and the residue was purified (0-30% EtOAc/hexane) by silica gel column chromatography to obtain Compound 30.

B. Compound 30 (216 mg, 1.0 mmol) was dissolved in CH$_2$Cl$_2$ (10 mL) in the presence of nitrogen, and a mixture of BBr$_3$ and CH$_2$Cl$_2$ was added thereto by syringe at −20° C. The reaction mixture was stirred at 20° C. for 1 h. After the addition of CH$_2$Cl$_2$ (20 mL), the mixture was washed with brine and then the organic phase was dried over Na$_2$SO$_4$. Finally, the organic solvent was evaporated, and the residue was purified (0-50% EtOAc/hexane) by silica gel column chromatography to obtain Compound 31. ES/MS: m/z: 203 [M+H]$^+$.

Difluoride 41 can also be prepared by the following method (Tetrahedron 2004, 60, 7731-7742):

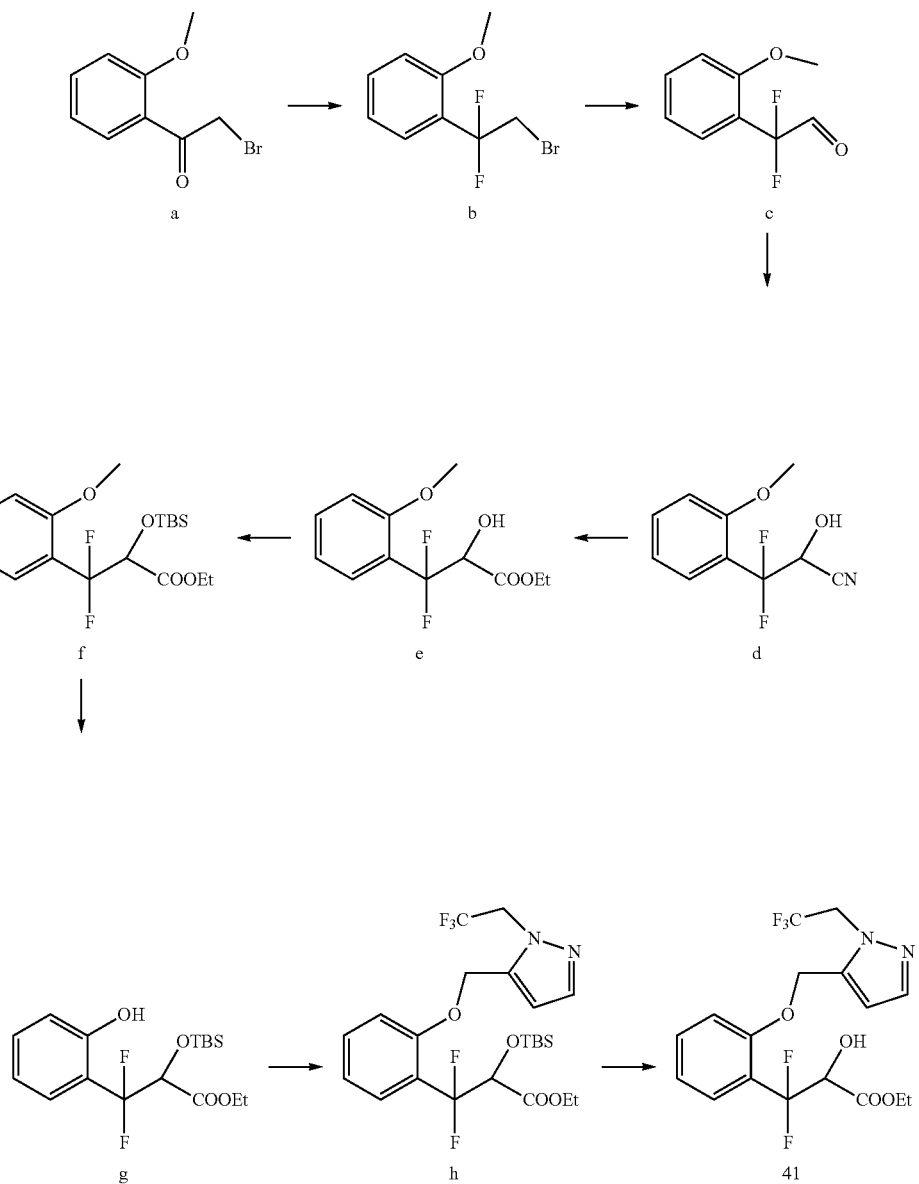

Example 11

Preparation of Compounds 32 and 33

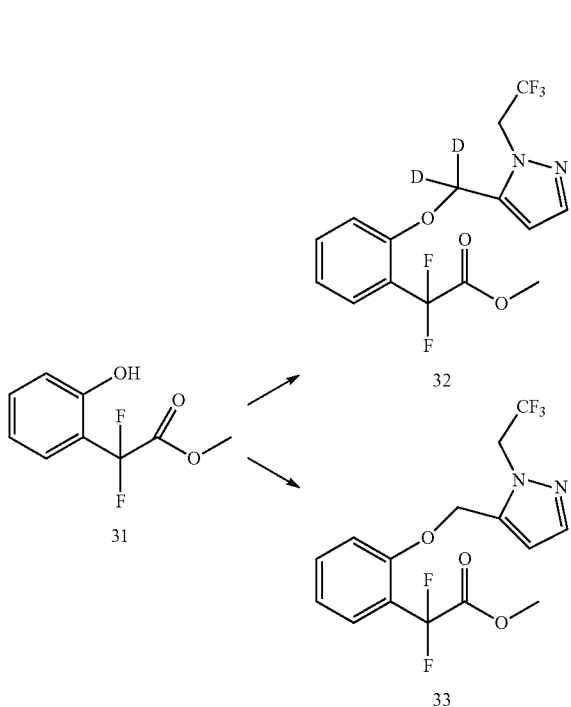

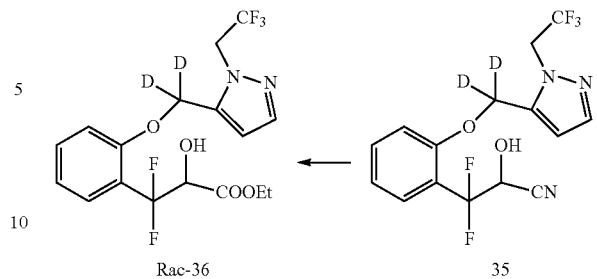

A. Compound 32: Compound 4 (182 mg, 1.0 mmol), Compound 31 (202 mg, 1.0 mmol) and PPh$_3$ (314 mg, 1.2 mmol) were dissolved in dry toluene (10 mL). Then DEAD (208 mg, 1.2 mmol) was added to the mixture and the mixture was stirred at 50° C. for 24 h. After the addition of EtOAc (50 mL), the mixture was washed with brine and then the organic phase was dried over Na$_2$SO$_4$. Finally, the organic solvent was evaporated, and the residue was purified (0-50% EtOAc/hexane) by silica gel column chromatography to obtain Compound 32. ES/MS: m/z: 367 [M+H]$^+$.

B. Compound 33: the same method as for the preparation of the compound 32 was employed except that the compound 31 was condensed with Compound 5 to obtain Compound 33. ES/MS: m/z: 365 [M+H]$^+$.

A. Compound 34: under nitrogen atmosphere, DIBAL (1.2 mL, 1 M/THF, 1.2 mmol) was added to a solution of compound 32 (366 mg, 1.0 mmol) in THF at −78° C. Then the mixture was stirred at −78° C. for 1 h. After the addition of EtOAc (50 mL), the mixture was washed with brine and then the organic phase was dried over Na$_2$SO$_4$. Finally, the organic solvent was evaporated, and the residue was purified (0-50% EtOAc/hexane) by silica gel column chromatography to obtain Compound 34.

B. Compound 35: a solution of Compound 34 (336 mg, 1 mmol) in THF (3 mL) was added to an aqueous (10 mL) solution of sodium sulfite (190 mg, 1 mmol), and the mixture was stirred vigorously at room temperature for 3 h. An aqueous (2 mL) solution of NaCN (98 mg, 2 mmol) was added to the above solution, and the reaction mixture was further stirred for 1 hour. The reaction mixture was extracted with EtOAc (100 mL) and then the organic phase was dried over Na$_2$SO$_4$. Finally, the organic solvent was evaporated, and the residue was purified (0-50% EtOAc/hexane) by silica gel column chromatography to obtain Compound 35. ES/MS: m/z: 364 [M+H]$^+$.

C. Compound Rac-36: after compound 35 (364 mg, 1 mmol) was dissolved in EtOH (1 mL), HCl gas was continuously and slowly introduced for 10 min. After 4 h of reaction, distilled water (5 mL) was added and stirred for 30 min. The reaction mixture was extracted with EtOAc (100 mL) and then the organic phase was dried over Na$_2$SO$_4$. Finally, the organic solvent was evaporated, and the residue was purified (0-80% EtOAc/hexane) by silica gel column chromatography to obtain Rac-36. m/z: 411 [M+H]$^+$.

Example 12

Preparation of Compound Rac-36

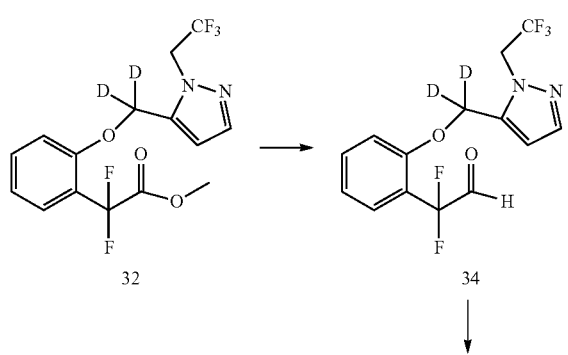

Example 13

Preparation of Compounds (2S)-37 and (2R)-38

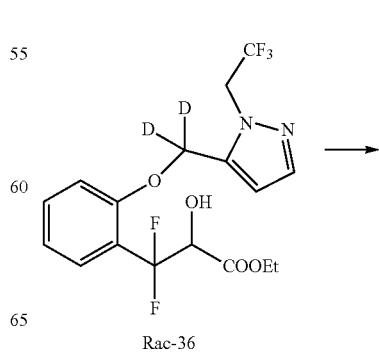

21
-continued

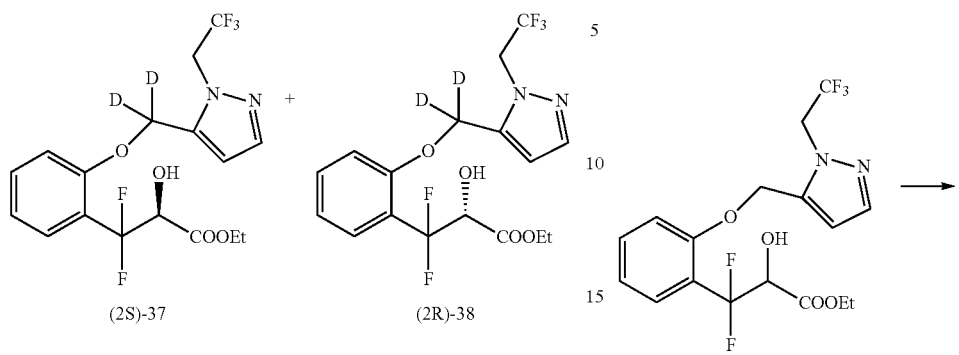

(2S)-37    (2R)-38

Compounds (2S)-37 and (2R)-38: Rac-36 were separated by chiral column to obtain (2S)-37 and (2R)-38, respectively.

Example 14

Preparation of Compound Rac-41

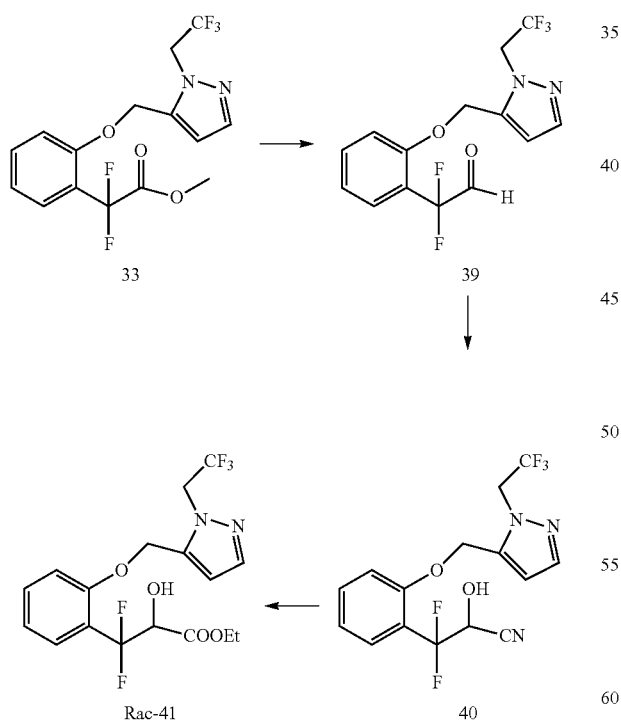

33    39

Rac-41    40

B. Compound Rac-41: the same method as for the preparation of the compound 36 was employed except that the compound 33 was selected an initial material to obtain Compound Rac-41. ES/MS: m/z: 409 [M+H]⁺.

22

Example 15

Preparation of Compounds (2S)-42 and (2R)-43

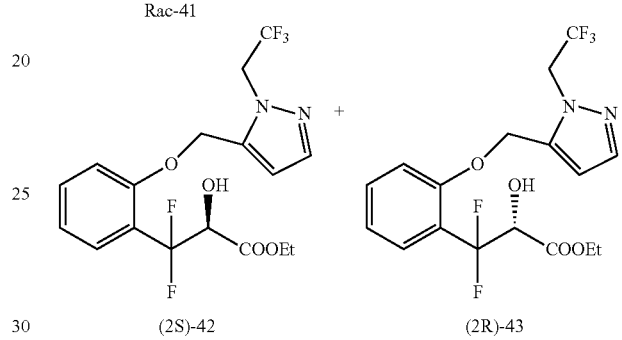

Rac-41

(2S)-42    (2R)-43

Compounds (2S)-42 and (2R)-43: Rac-41 were separated by chiral column to obtain (2S)-42 and (2R)-43, respectively.

Example 16

Preparation of Compound 46

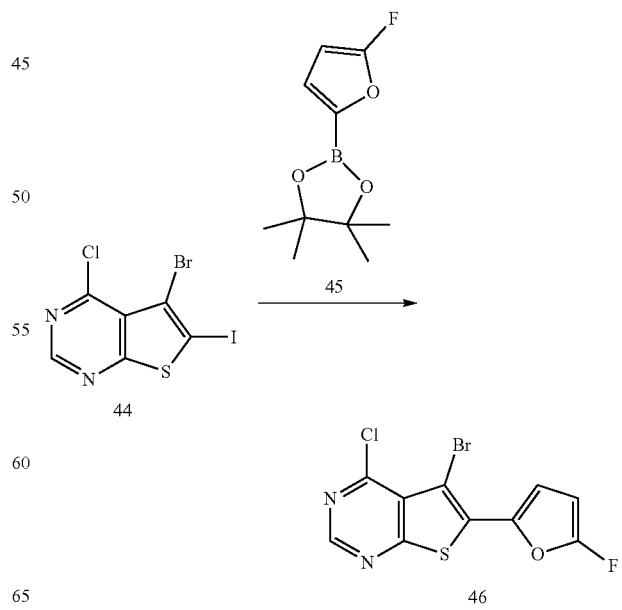

44

46

A. Both Compound 44 and Reagent 45 were prepared according to the method disclosed in WO 2015/097123.

B. Compound 44 (3.75 g, 10.0 mmol), reagent 45 (8.48 g, 40 mmol), CsCO$_3$ (6.52 g, 20.0 mmol), Pd(OAc)$_2$ (112 mg, 0.5 mmol), tBuX-Phos (477 Mg, 1 mmol) was added to THF (33 mL) and distilled water (13 mL). The reaction mixture was stirred at 70° C. for 20 h. Then THF was evaporated, and the crude solid was collected by filtration. Finally, the residue was purified (0-80% EtOAc/hexane) by silica gel column chromatography to obtain Compound 46. ES/MS: m/z: 332 [M+H]$^+$.

Example 17

Preparation of Compound 47

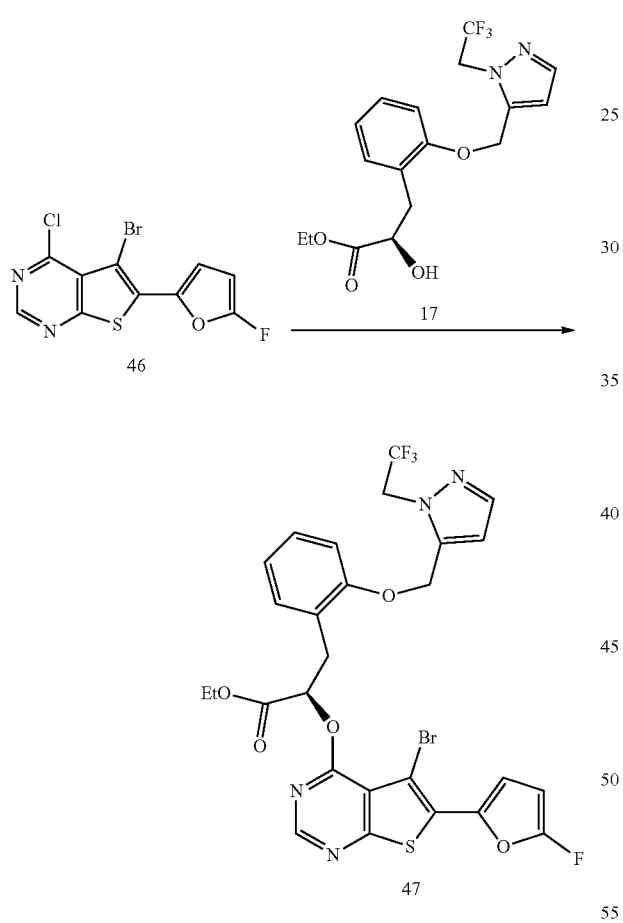

Compound 46 (331 mg, 1 mmol), compound 17 (411, mg, 1.1 mmol) and CsCO$_3$ (579 mg, 3 mmol) was added to t-BuOH (10 mL) and stirred at 70° C. for 24 h. Then the solvent was evaporated and distilled water (10 mL) was added. After the pH of the solution was adjusted to 8 with 1N HCl, CH$_2$Cl$_2$ was used to extract organics that was then dried over Na$_2$SO$_4$. Subsequently, the organic solvent was evaporated, and the residue was purified by silica gel column chromatography to obtain Compound (2S)-47. ES/MS: m/z: 669 [M+H]$^+$.

The following intermediates 48-68 were obtained with the same method as above:

| Formula | m/z |
| --- | --- |
| 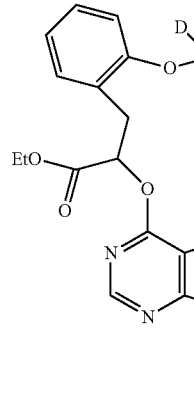 48 | 671 |
| 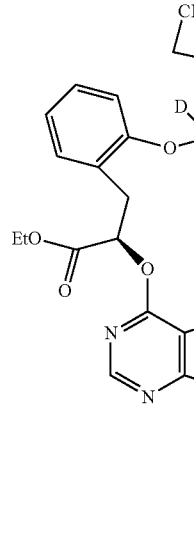 49 | 671 |
| 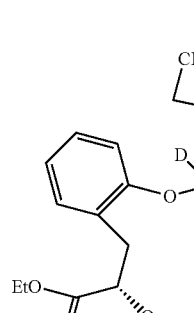 50 | 671 |

| Formula | m/z |
|---|---|
| 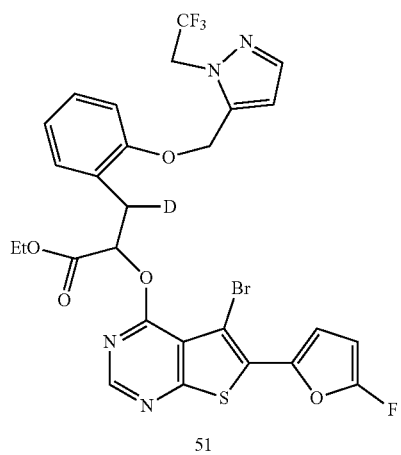 [SMILES: [2H]C(c1ccccc1OCc1ccnn1CC(F)(F)F)C(Oc1ncnc2sc(-c3ccc(F)o3)c(Br)c12)C(=O)OCC] 51 | 670 |
| 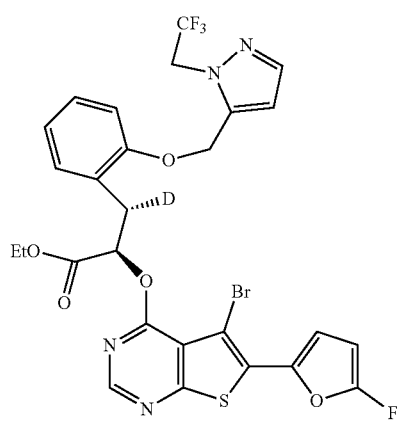 52 | 670 |
| 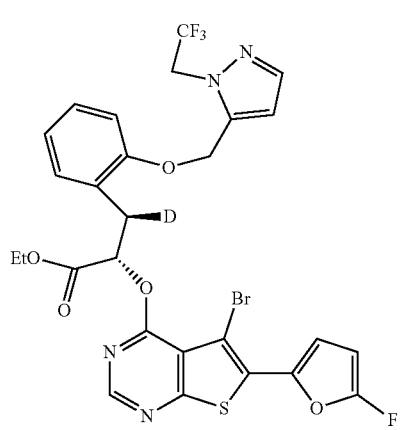 53 | 670 |
| 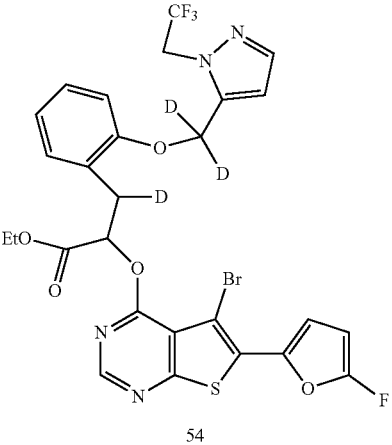 [SMILES: [2H]C(c1ccccc1OC([2H])([2H])c1ccnn1CC(F)(F)F)C(Oc1ncnc2sc(-c3ccc(F)o3)c(Br)c12)C(=O)OCC] 54 | 672 |
| 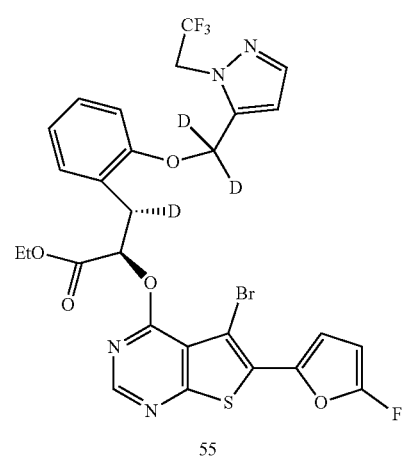 [SMILES: [2H][C@@H](c1ccccc1OC([2H])([2H])c1ccnn1CC(F)(F)F)[C@@H](Oc1ncnc2sc(-c3ccc(F)o3)c(Br)c12)C(=O)OCC] 55 | 672 |
| 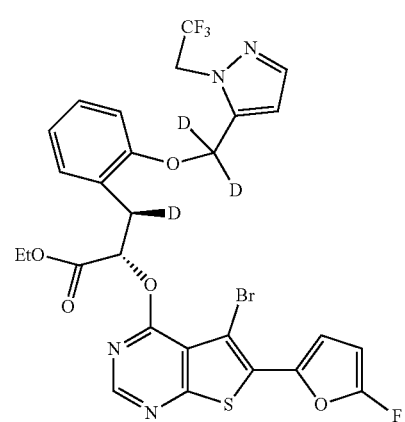 56 | 672 |

| 27 -continued | |
|---|---|
| Formula | m/z |
| 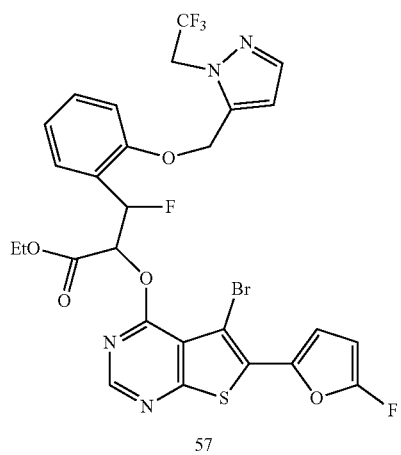 [SMILES: CCOC(=O)C(Oc1ncnc2sc(-c3ccc(F)o3)c(Br)c12)C(F)c1ccccc1OCc1ccnn1CC(F)(F)F] 57 | 687 |
| 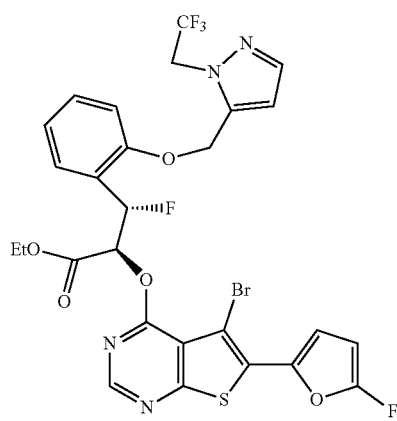 58 | 687 |
| 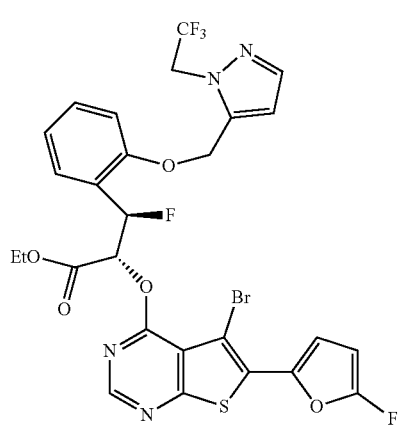 59 | 687 |
| 28 -continued | |
|---|---|
| Formula | m/z |
| 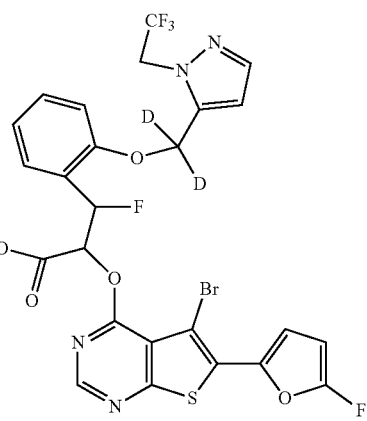 60 | 689 |
| 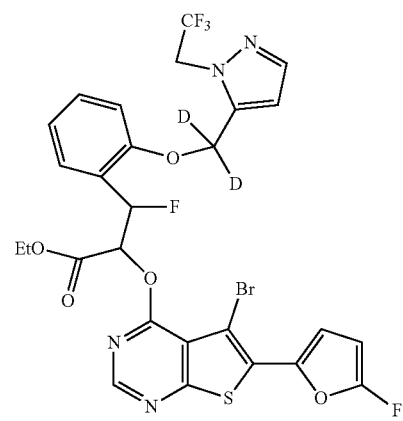 61 | 689 |
| 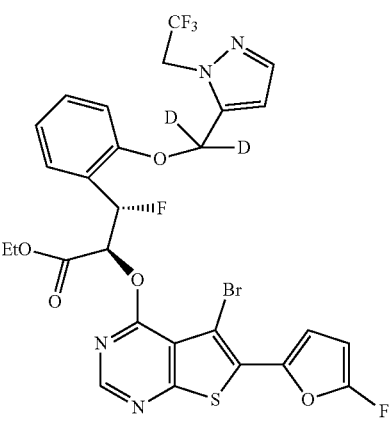 62 | 689 |

| Formula | m/z |
|---|---|
| 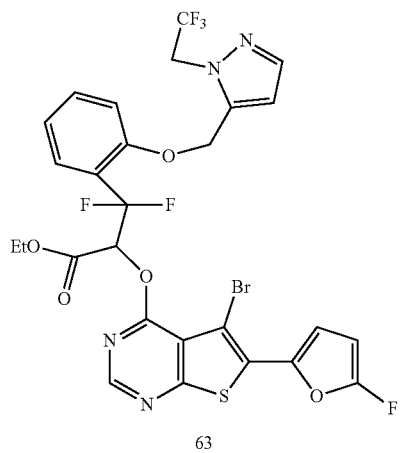 [SMILES: CCOC(=O)C(Oc1ncnc2sc(-c3ccc(F)o3)c(Br)c12)C(F)(F)c1ccccc1OCc1ccnn1CC(F)(F)F] 63 | 705 |
| 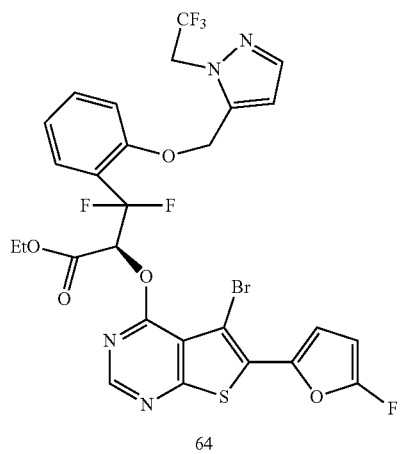 [SMILES: CCOC(=O)[C@H](Oc1ncnc2sc(-c3ccc(F)o3)c(Br)c12)C(F)(F)c1ccccc1OCc1ccnn1CC(F)(F)F] 64 | 705 |
| 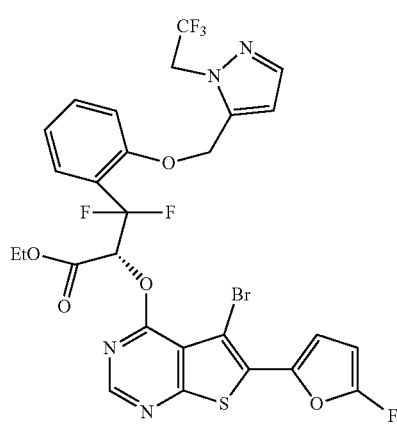 65 | 705 |
| Formula | m/z |
|---|---|
| 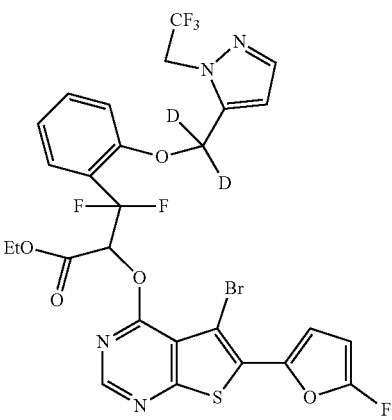 66 | 707 |
| 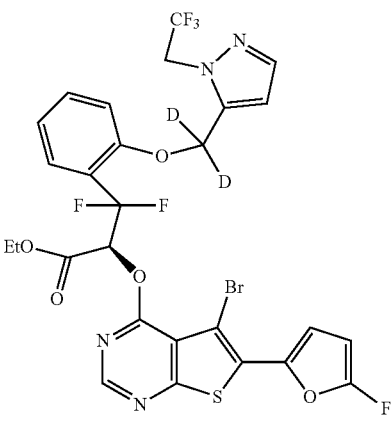 67 | 707 |
| 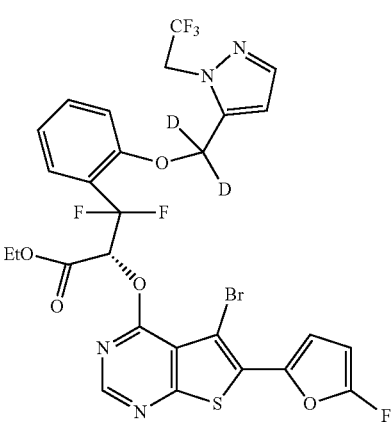 68 | 707 |

| Formula | m/z |
|---|---|

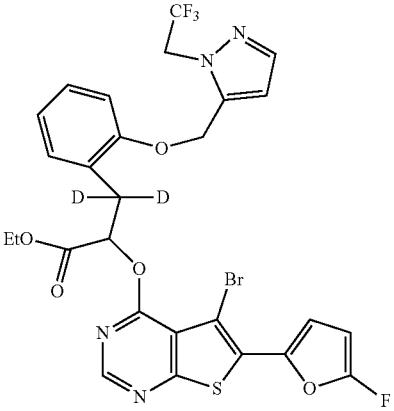

XIa

Example 18

Preparation of Compound 69

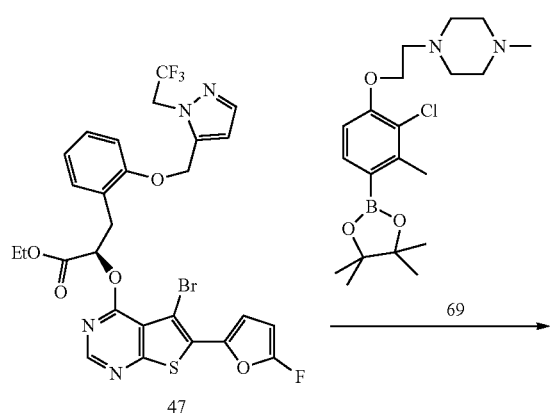

A. Compound 46 was prepared.

B. Compound 47 (66.9 g, 0.1 mmol), reagent 69 (158 mg, 0.40 mmol), CsCO₃ (65 g, 0.20 mmol), Pd(OAc)₂ (30 mg), ᵗBuX-Phos (47.7 Mg, 0.1 mmol) was added to THF (3 mL) and distilled water (1.5 mL). The reaction mixture was stirred at 70° C. for 20 h. Then THF was evaporated, and the crude solid filtered from the solution was collected. Finally, the residue was purified by high performance liquid chromatography (HPLC) to obtain Compound 70. ES/MS: m/z: 857 [M+H]⁺.

The following intermediates 71-91 were obtained according to the operations as above:

| Formula | m/z |
|---|---|

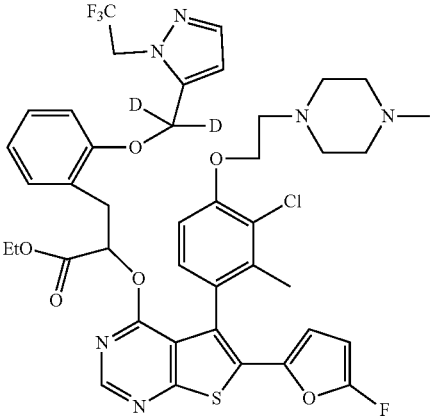

-continued
| Formula | m/z |
|---|---|
| 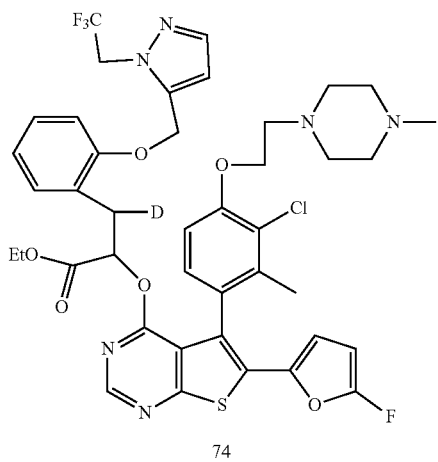 [SMILES: [2H]C(c1ccccc1OCc1ccnn1CC(F)(F)F)C(Oc1ncnc2sc(-c3ccc(F)o3)c(-c3ccc(OCCN4CCN(C)CC4)c(Cl)c3C)c12)C(=O)OCC] 74 | 858 |
| 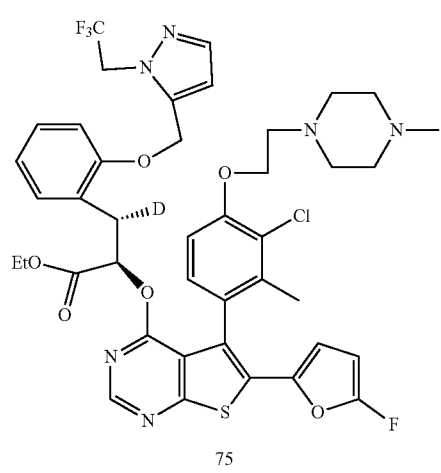 [SMILES: [2H][C@@H](c1ccccc1OCc1ccnn1CC(F)(F)F)[C@@H](Oc1ncnc2sc(-c3ccc(F)o3)c(-c3ccc(OCCN4CCN(C)CC4)c(Cl)c3C)c12)C(=O)OCC] 75 | 858 |
| 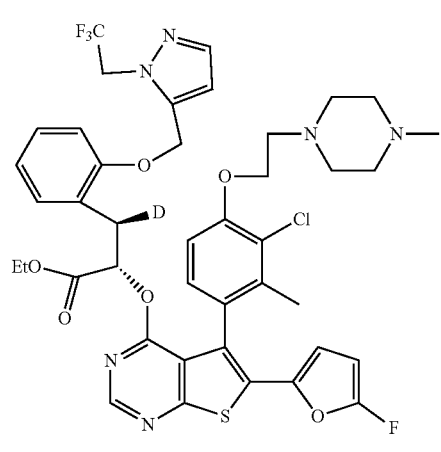 76 | 858 |
-continued
| Formula | m/z |
|---|---|
| 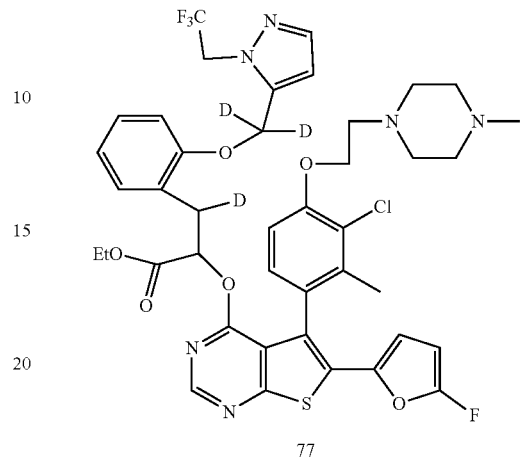 77 | 860 |
| 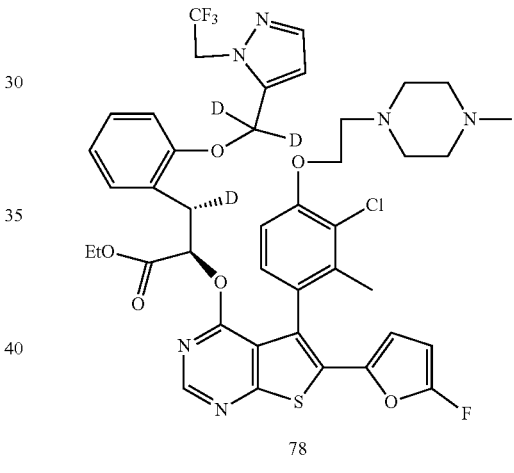 78 | 860 |
| 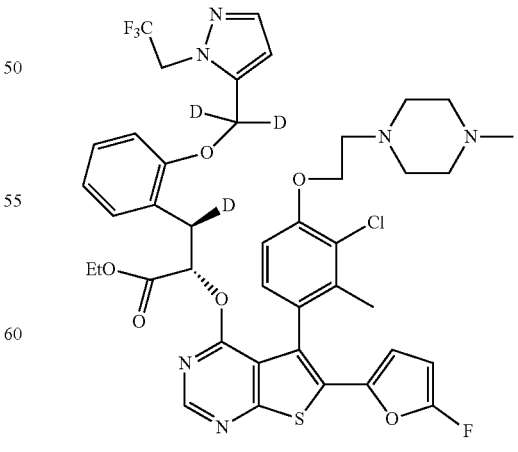 79 | 860 |

TABLE 35-continued
| Formula | m/z |
|---|---|
| 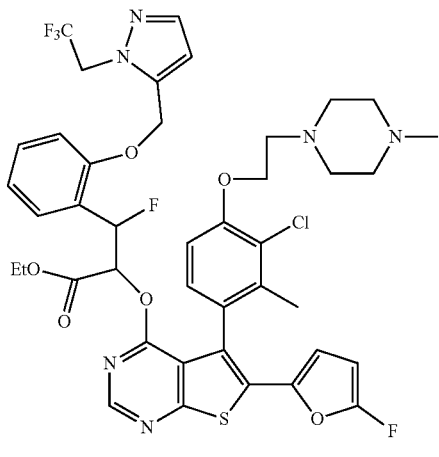 80 | 875 |
| 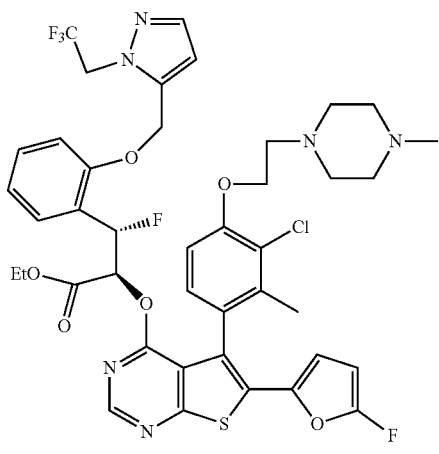 81 | 875 |
| 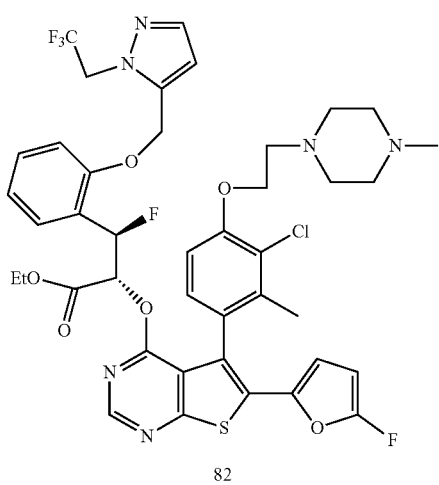 [SMILES: CCOC(=O)[C@@H](Oc1ncnc2sc(-c3ccc(F)o3)c(-c3ccc(OCCN4CCN(C)CC4)c(Cl)c3C)c12)[C@H](F)c1ccccc1OCc1ccnn1CC(F)(F)F] 82 | 875 |
TABLE 36-continued
| Formula | m/z |
|---|---|
| 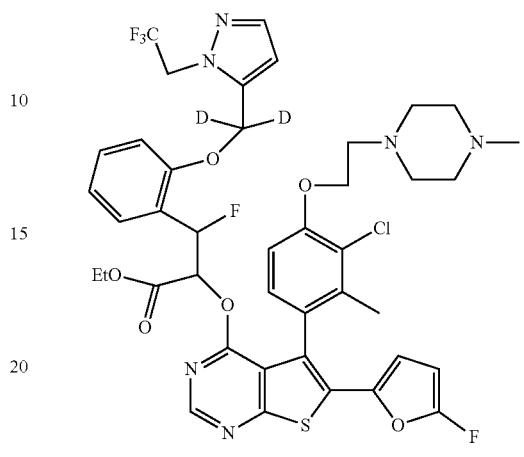 83 | 877 |
| 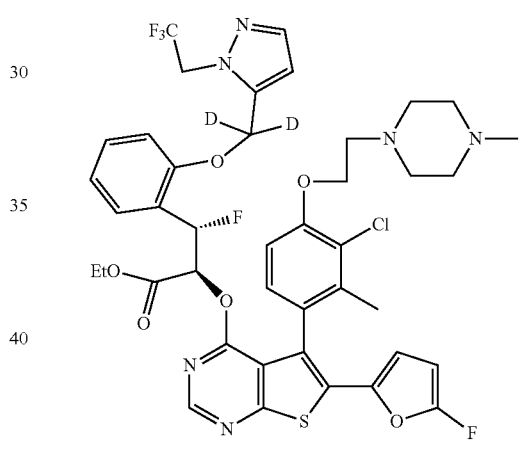 84 | 877 |
| 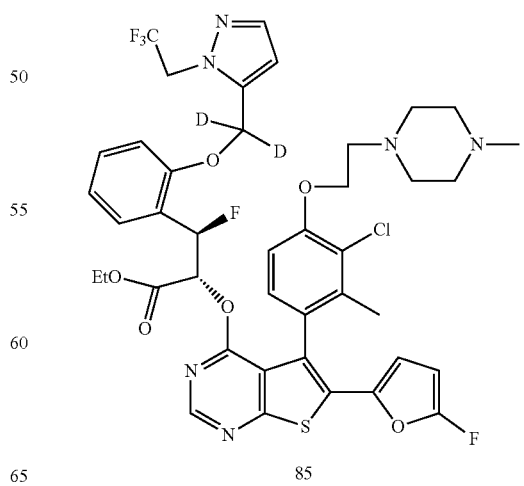 85 | 877 |

| Formula | m/z |
|---|---|
| 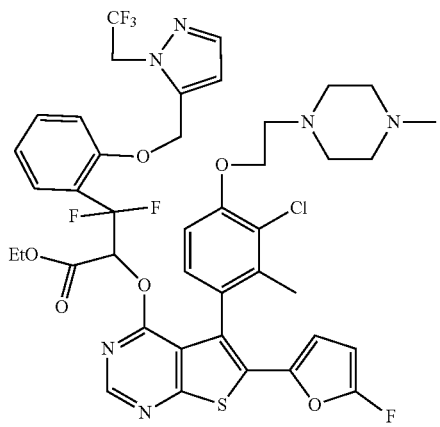 86 | 893 |
| 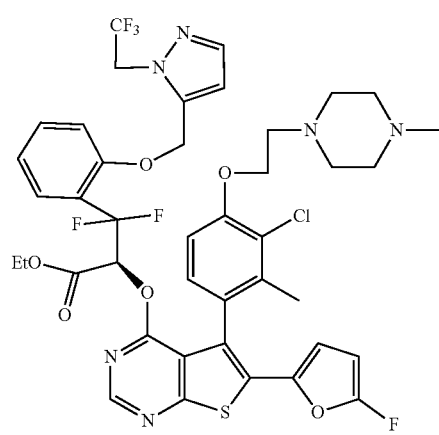 87 | 893 |
| 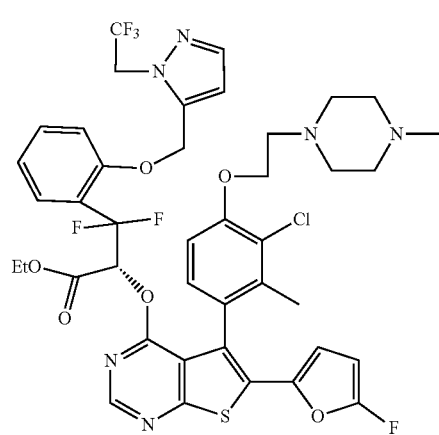 88 | 893 |
| Formula | m/z |
|---|---|
| 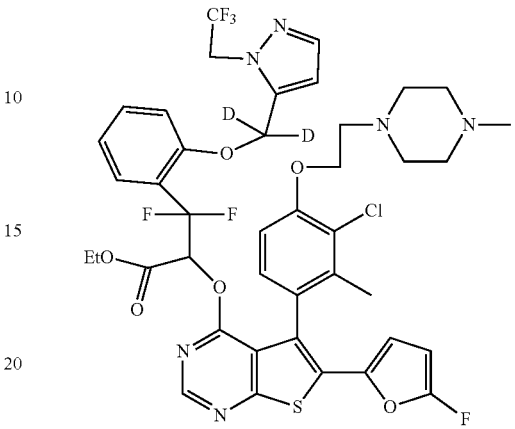 89 | 895 |
| 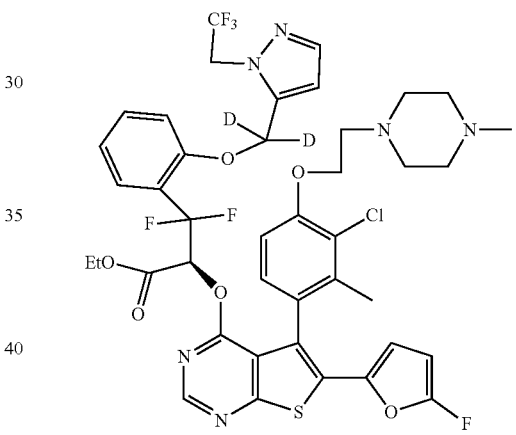 90 | 895 |
| 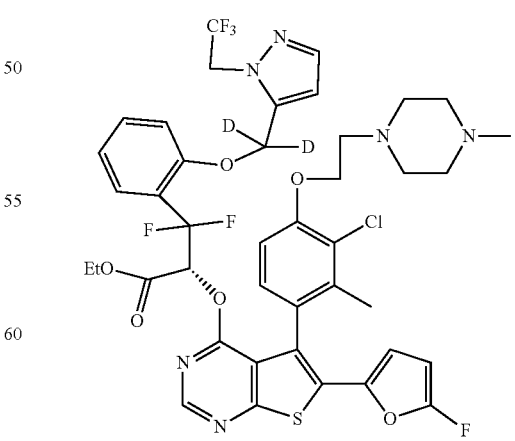 91 | 895 |

| Formula | m/z |
|---|---|

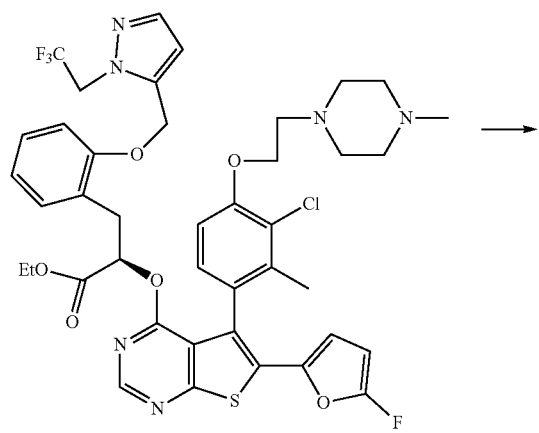

XIb

Example 19

Preparation of Compound II

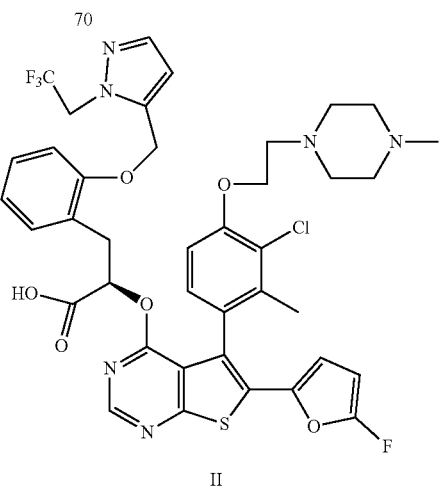

70

II

Compound 70 (86 mg, 0.1 mmol) and 10 eq. LiOH×H₂O was dissolved in H₂O: Dioxane (10 mL/mmol) and stirred at room temperature for 24 h. The mixture was acidified with HCl solution and extracted with EtOAc.

After the solution was acidified with 1M HCl, the organics was extracted with EtOAc, and then the organic phase was dried over Na₂SO₄. Subsequently, the organic solvent was evaporated, and the crude product was purified by HPLC (the mobile phase is 25 mM NH₄HCO₃ solution and MeCN) to obtain Compound II. ES/MS: m/z: 829 [M+H]⁺.

The following intermediates IV-X and 92-105 were obtained according to the operations as above:

| Formula | m/z |
|---|---|
|  | 831 |

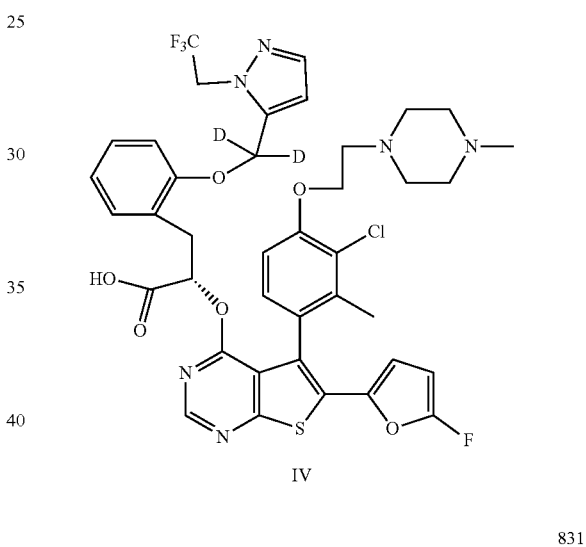

IV

831

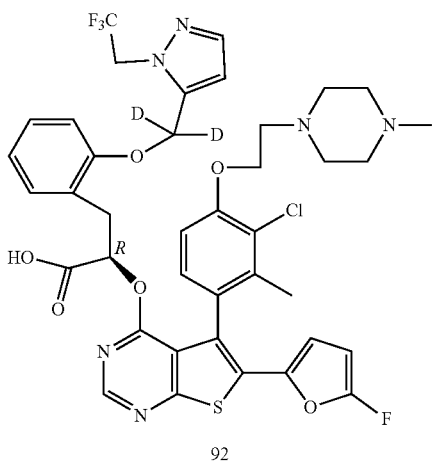

92

| Formula | m/z |
|---|---|
| 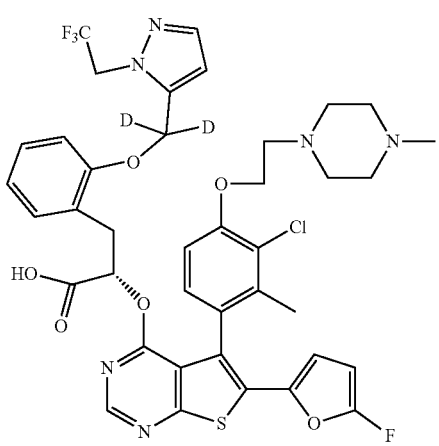 93 | 831 |
| 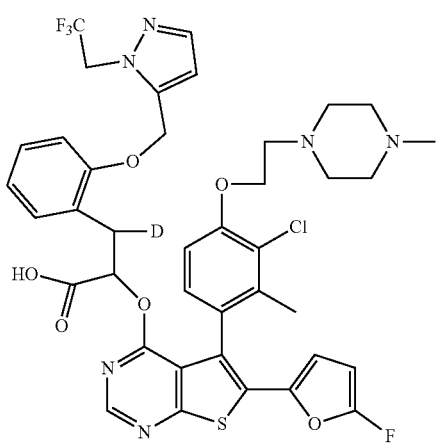 V | 830 |
| 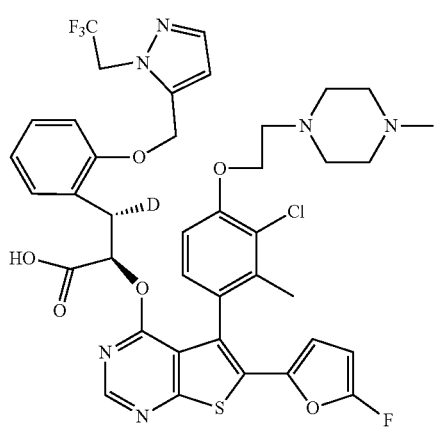 94 | 830 |
| Formula | m/z |
|---|---|
| 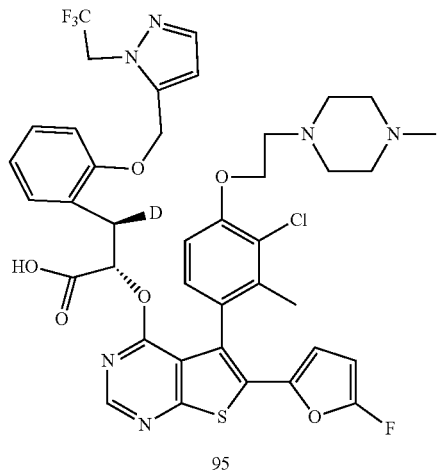 95 | 830 |
| 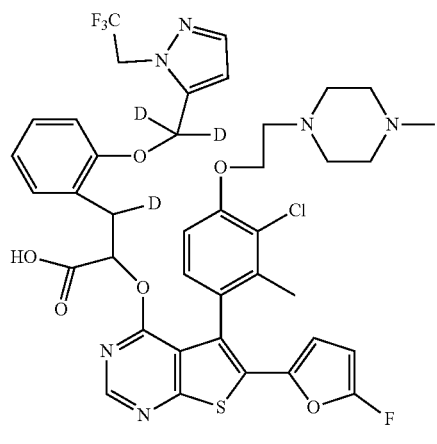 VI | 832 |
| 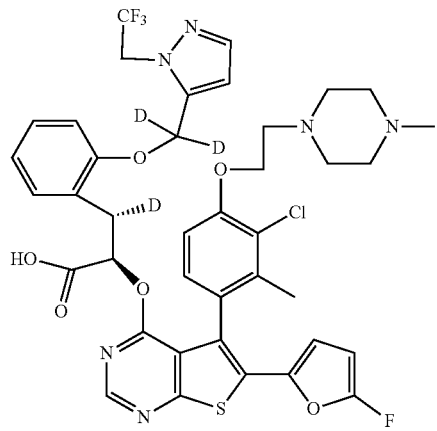 96 | 832 |

| Formula | m/z |
|---|---|
| 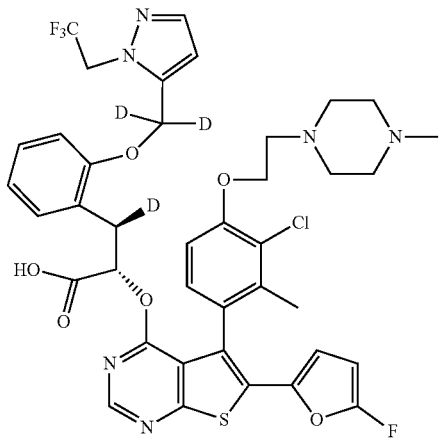97 | 832 |
| 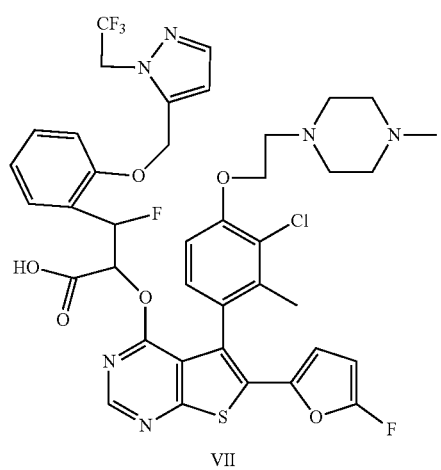VII | 847 |
| 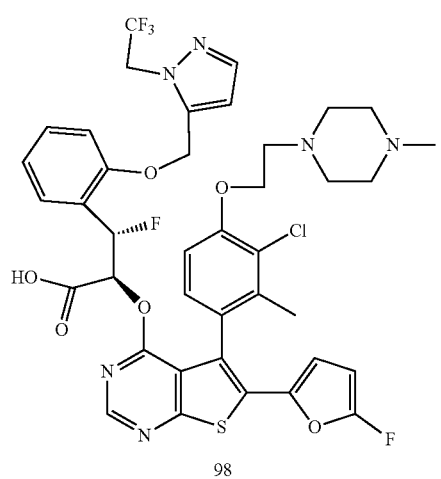98 | 847 |
| Formula | m/z |
|---|---|
| 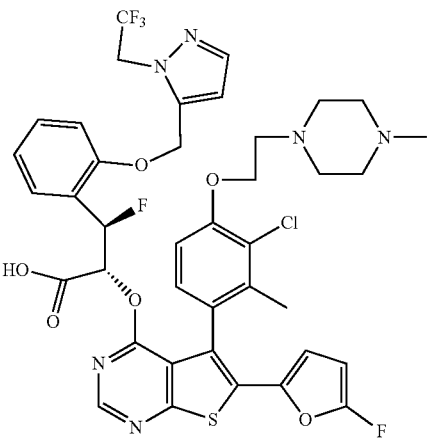99 | 847 |
| 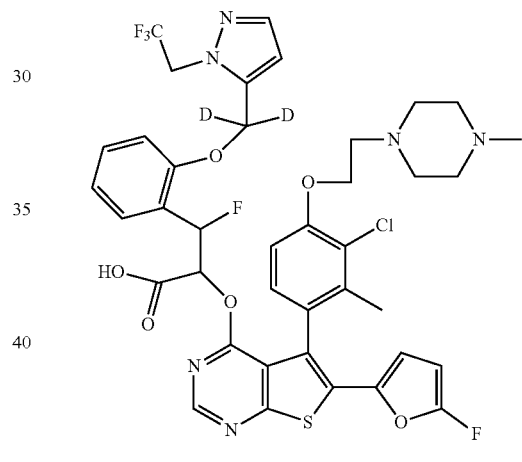VIII | 849 |
| 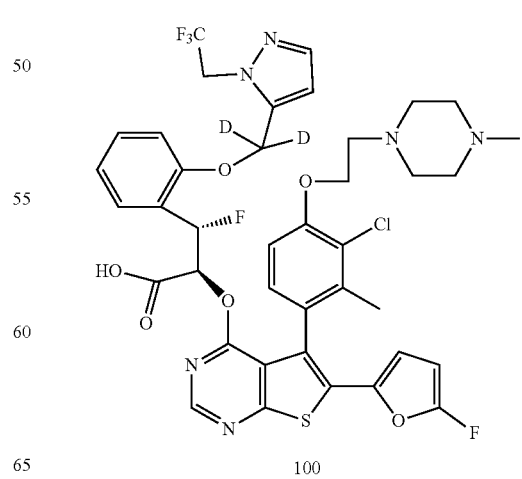100 | 849 |

-continued
| Formula | m/z |
|---------|-----|
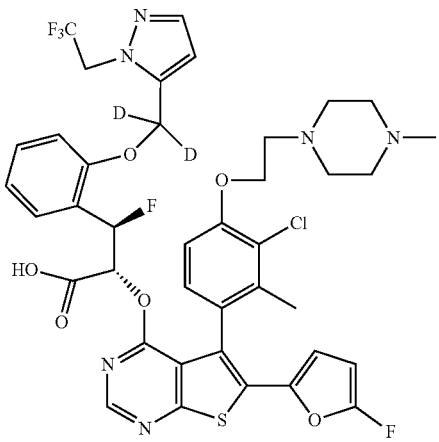
101
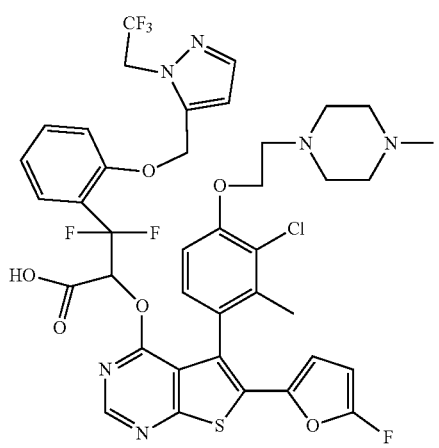
IX
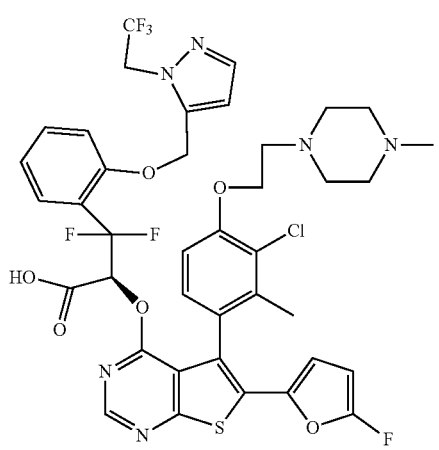
102
-continued
| Formula | m/z |
|---------|-----|
|  | 865 |
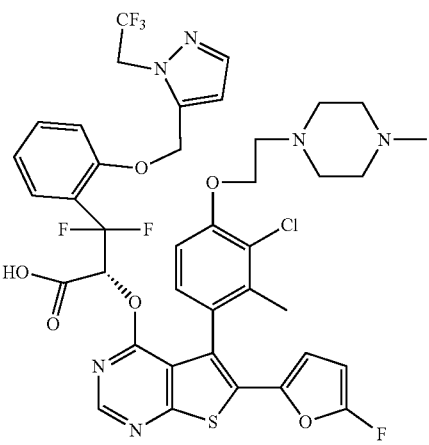
103
|  | 867 |
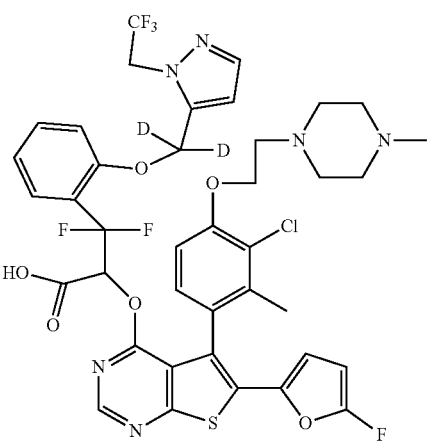
X
|  | 867 |
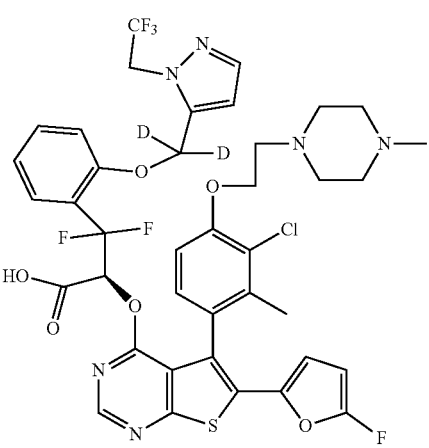
104

| Formula | m/z |
|---|---|
| (structure 105) | 105 |
| (structure XI) | XI |

Example 20

Biological Test and Pharmacological Study

I. Determination of the Degree of Inhibition of Mcl-1 Activity Using Fluorescence Polarization Technology.

The relative bonding capacity of each compound was determined by a fluorescence polarization (FP) technology. This method utilizes a fluorescently labeled ligand to bind (fluorescein-βAla-Ahx-A-REIGAQLRRMADDLNAQY-OH; 2765 MW) to the Mcl-1 protein, resulting in an anisotropic polarization increase, which is shown in millivolts (MP) units on the reader. The addition of a compound that is competitively bonded to the binding site of the ligand will result in a greater proportion of unbound ligand in the system, which is the conclusion from the reduction in mP value.

Each compound was dissolved in DMSO and then serially diluted 11 times. 2 μL diluted solution was then transferred to a flat-bottomed and low-bonded 384-well plate (final concentration of 5% DMSO). The 38 μL buffer (20 mM $Na_2PO_4$, 1 mM EDTA, 50 mM NaCl, pH 7.4) and fluorescein-labeled ligand (final concentration of 10 nM) were added, followed by the addition of Mcl-1 protein (final concentration of 10 nM).

The 384-well plate was incubated for 2 hours at room temperature before measuring the polarization value FP and calculating the polarization value mP using a Biomek Synergy 2 microplate reader (Ex.528 nm, Em.640 nM, Cut off 510 nM). The bonding amount that is reduced due to the increase in the dosage of each compound is expressed as: the percentage of reduced mP values between "only 5% DMSO" and "100% inhibition" (50 μM unlabeled ligand) was compared for the same compound at the same assay time. The data from 11 points was plotted as a dose response curve using a four-parameter logistic model in XL-fit software (XL-fit Software). The half maximal inhibitory concentration was defined based on the reduced 50% mP (Table 1, IC50).

II. In Vitro Cytotoxicity

Multiple myeloma tumor cells (H929) were used for toxicity studies, and the cells were distributed in microtiter plates and exposed to the compounds tested for 48 hours. Cell viability was measured by MTT Thiazole Blue Colorimetric Assay (Cancer Research, 1987, 47, 939-942), and the results of the assay are expressed as $IC_{50}$ (Table 1, the concentration at which the compound inhibits 50% of cell viability). + indicates $IC_{50}$ is above 10 nM; ++ indicates $IC_{50}$ is 1-10 nM; +++ indicates $IC_{50}$ is below 1 nM.

TABLE 1

Inhibition on Mcl-1 activity and toxicity to H929 cells of compounds

| Compounds | $IC_{50}$ of Mcl-1 | $IC_{50}$ of H929 |
|---|---|---|
| II | ++ | + |
| 102 | +++ | + |
| 103 | ++ | + |
| 106 | +++ | + |
| 107 | +++ | + |
| 110 | +++ | + |
| 111 | ++ | + |
| XI | +++ | + |

The results in Table 1 indicate that some of the compounds disclosed in the disclosure, including monofluorides, difluorides, and deuterates, have the same or better effect and selectivity for inhibiting Mcl-1 activity than Compound II.

It will be obvious to those skilled in the art that changes and modifications may be made, and therefore, the aim in the appended claims is to cover all such changes and modifications.

What is claimed is:

1. A compound having a formula (I), or a pharmaceutically acceptable salt, or a solvate thereof:

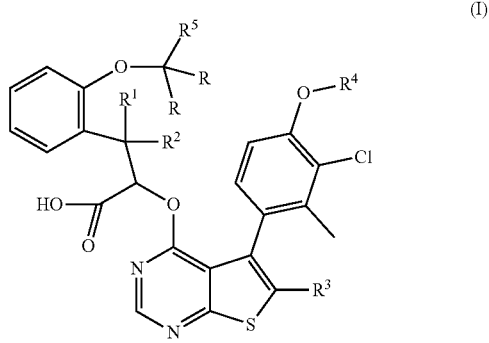

wherein:

R represents hydrogen (H) or deuterium (D);

$R^1$ and $R^2$ independently, at each occurrence, represent H, D, F, Cl, I, cyano group (CN), or $N_3$, and when R represents H, $R^1$ and $R^2$ do not synchronously represent H; and $R^3$, $R^4$ and $R^5$ independently, at each occurrence, represent an alkyl group, a cycloalkyl group, a heterocyclic group, an aromatic ring group, or a heteroaryl ring group.

2. The compound of claim 1, wherein $R^3$, $R^4$ and $R^5$ independently, at each occurrence, represent a $C_{1-5}$ alkyl group, a $C_{3-6}$ cycloalkyl group, a nitrogen-containing or oxygen-containing saturated or unsaturated five- or six-membered heterocyclic ring, or a phenyl group.

3. The compound of claim 1, wherein the compound has a formula (III):

(III)

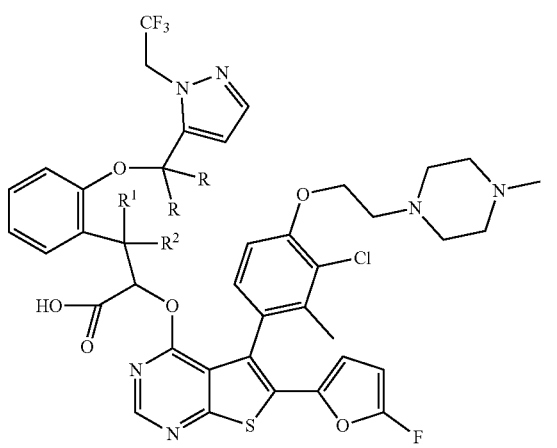

R represents hydrogen (H) or deuterium (D); and $R^1$ and $R^2$ independently, at each occurrence, represent H, D, F, Cl, I, CN, or $N_3$, and when R and $R^1$ or $R^2$ represent H, $R^2$ or $R^1$ does not represent H.

4. The compound of claim 1, wherein the compound has a formula of:

IV

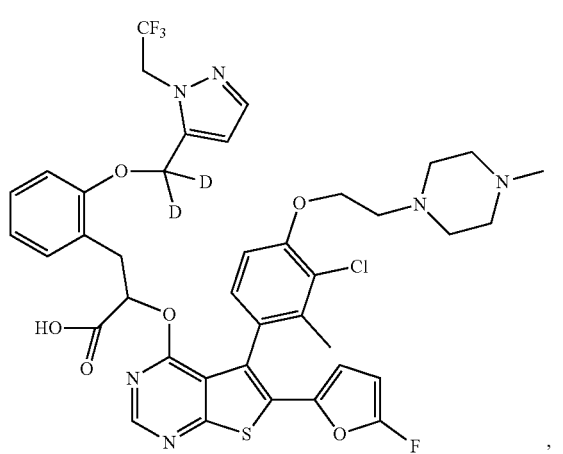

V

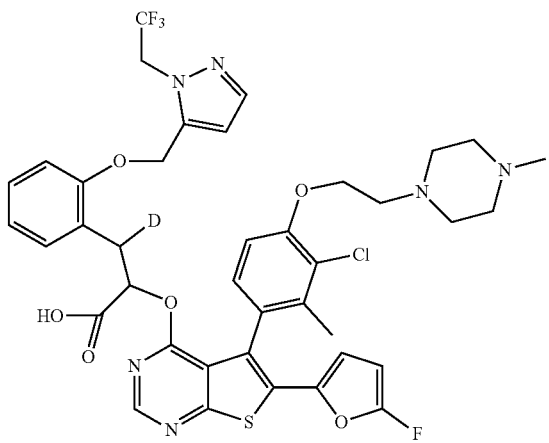

VI

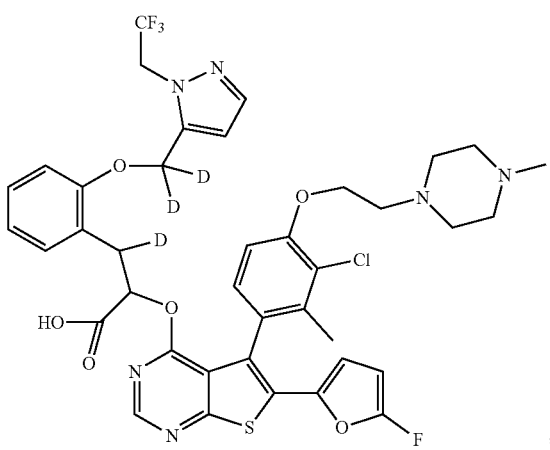

VII

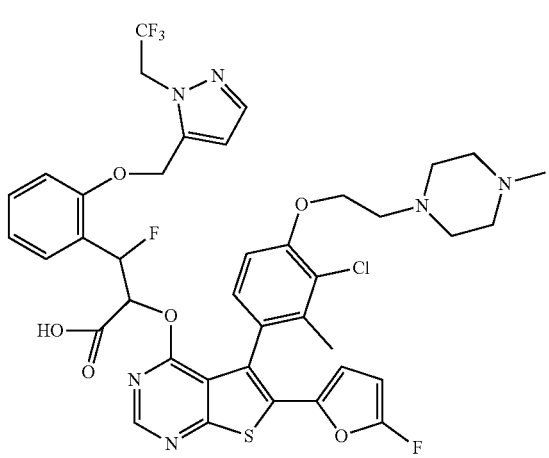

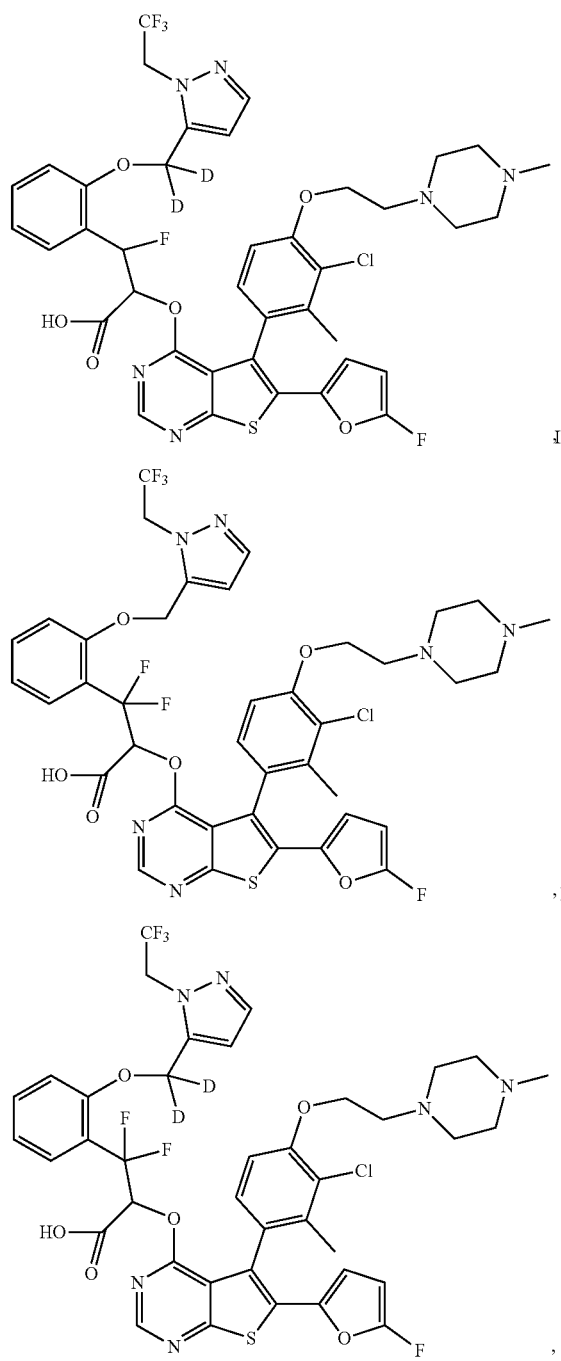

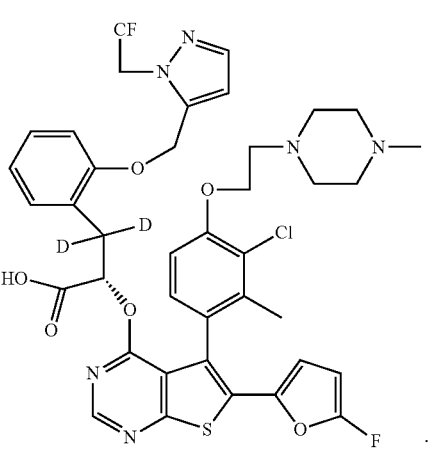

5. A method of preparing a pharmaceutical composition for treatment of a tumor, the method comprising mixing the compound of claim 1, or a pharmaceutically acceptable salt, solvate thereof with a pharmaceutically acceptable carrier and a diluent.

6. The method of claim 5, wherein the tumor is selected from the group consisting of acute myeloid leukemia, lymphoma and multiple myeloma, melanoma, lung and breast cancer, brain tumor, adenocarcinoma, liver cancer, colorectal cancer, medullary thyroid carcinoma, glioma, neuroblastoma, kidney tumor ovarian cancer, and prostate cancer.

7. A pharmaceutical composition, comprising: the compound of claim 1, or a pharmaceutically acceptable salt, solvate thereof; a pharmaceutically acceptable carrier; and a diluent.

8. The pharmaceutical composition of claim 7, further comprising an anticancer agent.

* * * * *